United States Patent [19]

Aburaki et al.

[11] Patent Number: 4,525,473
[45] Date of Patent: * Jun. 25, 1985

[54] CEPHALOSPORINS

[75] Inventors: Shimpei Aburaki, Tokyo; Hajime Kamachi, Urayasu; Yukio Narita; Jun Okumura, both of Yokohama; Takayuki Naito, Kawasaki, all of Japan

[73] Assignee: Bristol-Myers Company, New York, N.Y.

[*] Notice: The portion of the term of this patent subsequent to Sep. 27, 2000 has been disclaimed.

[21] Appl. No.: 480,602

[22] Filed: Mar. 30, 1983

[51] Int. Cl.³ .................. A61K 31/545; C07D 501/46
[52] U.S. Cl. ....................................... 514/202; 544/22
[58] Field of Search ........................... 544/22; 424/246

[56] References Cited

U.S. PATENT DOCUMENTS

| | | | |
|---|---|---|---|
| 4,168,309 | 9/1979 | Ayres et al. | 544/22 |
| 4,278,671 | 7/1981 | Ochiai et al. | 544/22 |
| 4,278,793 | 7/1981 | Durckheimer et al. | 544/22 |
| 4,406,899 | 9/1983 | Aburaki et al. | 544/22 |

FOREIGN PATENT DOCUMENTS

| | | |
|---|---|---|
| 2805655 | 8/1978 | Fed. Rep. of Germany . |
| 3311300 | 9/1983 | Fed. Rep. of Germany . |
| 1399086 | 6/1975 | United Kingdom . |

Primary Examiner—Donald G. Daus
Assistant Examiner—Mary E. Ceperley
Attorney, Agent, or Firm—Richard R. Lloyd

[57] ABSTRACT

Compounds of the formula

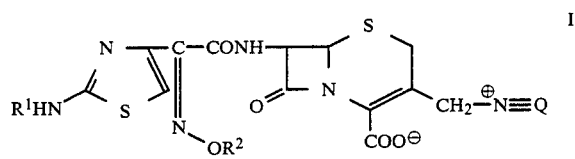

wherein $R^1$ is hydrogen or a conventional amino-protecting group, $R^2$ is a straight or branched chain alkyl, alkenyl or alkynyl containing from 1 to 4 carbon atoms, and

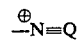

is a quaternary ammonio group as described herein, and nontoxic pharmaceutically acceptable salts, physiologically hydrolyzable esters and solvates thereof, as well as processes for their preparation, are disclosed. The compounds in which $R^1$ is hydrogen are potent antibacterial agents.

48 Claims, No Drawings

CEPHALOSPORINS

SUMMARY OF THE INVENTION

This invention relates to novel cephalosporin derivatives of the formula

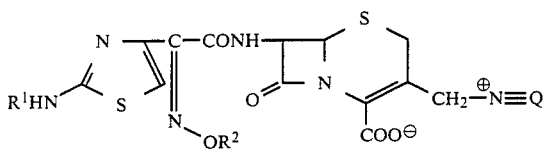

I wherein $R^1$ is hydrogen or a conventional amino-protecting group, $R^2$ is a straight or branched chain alkyl, alkenyl or alkynyl group containing from 1 to 4 carbon atoms, and

is a quaternary ammonio group as described below, and to nontoxic pharmaceutically acceptable salts, physiologically hydrolyzable esters and solvates thereof.

DESCRIPTION OF THE PRIOR ART

U.K. Patent Specification No. 1,399,086 contains a generic disclosure encompassing a vast number of cephalosporins of the formula

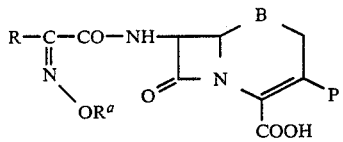

B wherein R is hydrogen or an organic group, $R^a$ is an etherifying monovalent organic group linked to the oxygen through a carbon atom, B is $>S$ or $>S\rightarrow O$, and P is an organic group. However, the 2-aminothiazol-4-yl group is not identified as an R substituent and there is no suggestion that P may be a fully or partially saturated nitrogen-containing ring which is attached to the 3-methyl moiety via its nitrogen atom and which contains an additional substituent on its nitrogen atom. U.S. Pat. No. 3,971,778 and its divisionals Nos. 4,024,133, 4,024,137, 4,064,346, 4,033,950, 4,079,178, 4,091,209, 4,092,477 and 4,093,803 have similar disclosures.

U.S. Pat. No. 4,278,793 contains a generic disclosure encompassing a vast number of cephalosporin derivatives of the formula

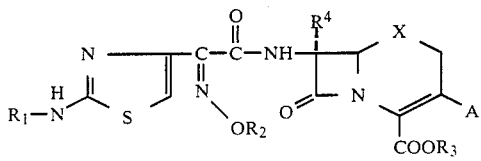

in which the variables $R_1$, $R_2$, $R_3$, $R_4$, X and A include generic definitions of the corresponding substituents of the compounds of Formula I claimed herein. However, in the 20 columns of definitions of the various substituent groups, the 78 page long table of structural formulae and the 225 examples, there is no disclosure that A may be a fully or partially saturated nitrogen-containing heterocyclic ring which is attached to the 3-methyl moiety via its nitrogen atom and which contains an additional substituent on its nitrogen atom. United Kingdom Patent Specification No. 1,604,971 is concordant thereto and has a substantially identical disclosure. Published United Kingdom Patent Application No. 2,028,305 A, although apparently not formally related, contains the same broad generic disclosure but exemplifies A only as hydrogen.

West German OLS 2,805,655 discloses 7-[2-(2-aminothiazol-4-yl)-2-(syn)methoxyiminoacetamido]cephalosporanic acid derivatives of the formula

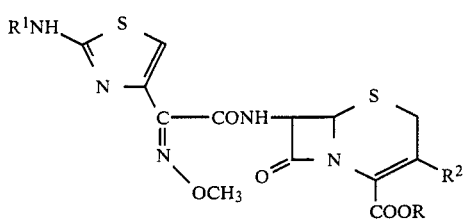

in which $R^1NH$ is an optionally protected amino group, $R^2$ is halogen or an optionally substituted hydroxyl, thiol or amino group, and COOR is an optionally esterified carboxyl group. It is also disclosed that, when $R^2$ is an amino group, it may be disubstituted and the substituents, taken together with the N atom, may form inter alia a pyrrolidino, morpholino or thiomorpholino group. However, there is no disclosure of an N-(substituted)pyrrolidinio, N-(substituted)morpholinio or N-(substituted)thiomorpholinio group (or of any other quaternary ammonio group). Further, its substituent $R^2$ cannot be connected to the 3-position via a methylene group.

U.S. Pat. No. 4,278,671 discloses 7-[2-(2-aminothiazol-4-yl)-2-(syn)-methoxyiminoacetamido]cephalosporin derivatives of the formula

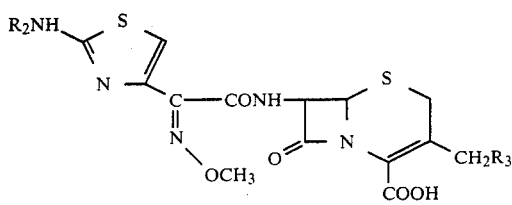

in which $R_2NH$ is an optionally protected amino group and $R_3$ is hydrogen or "the residue of a nucleophilic compound". The term "the residue of a nucleophilic compound" is broadly defined and it is then stated that $R^3$ "may alternatively be a quaternary ammonium group". Pyridinium, variously substituted pyridinium, quinolinium, picolinium and lutidinium are disclosed as quaternary ammonium groups. There is no suggestion that the quaternary ammonium group may consist of a fully or partially saturated nitrogen-containing heterocyclic ring system which is bound via its nitrogen atom and which contains an additional substituent on its nitrogen atom. United Kingdom Patent Specification No. 1,581,854 is concordant thereto and has a substantially identical disclosure. Other patents to the same patentee, which are not formally related but which have similar disclosures, include U.S. Pat. No. 4,098,888 and its divisionals U.S. Pat. Nos. 4,203,899, 4,205,180 and 4,298,606, and United Kingdom Patent Specification No. 1,536,281.

U.S. Pat. No. 4,168,309 discloses cephalosporin derivatives of the formula

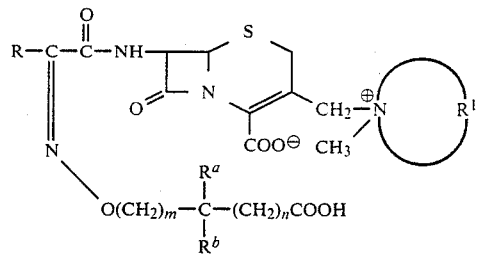

wherein R is phenyl, thienyl or furyl, $R^a$ and $R^b$ are hydrogen, (lower)alkyl, (lower)alkenyl, $C_{1-4}$ alkyl, $C_{2-4}$ alkenyl, $C_{3-7}$ cycloalkyl, phenyl, naphthyl, thienyl, furyl, carboxy, $C_{2-5}$ alkoxycarbonyl or cyano, or $R^a$ and $R^b$, taken together with the carbon atom to which they are attached, form a $C_{3-7}$ cycloalkylidene or cycloalkenylidene ring, m and n are each 0 or 1 such that the sum of m and n is 0 or 1, and $R^1$, taken together with the nitrogen atom to which it is attached, may be a saturated or partially saturated 4–10 membered heterocyclic ring which may contain one or more further heteroatoms selected from O, N and S, and which may be substituted with one of several specified substituents, or the heterocyclic ring may be fused to a benzene ring. Examples of the heterocyclic ring formed by $R^1$ and the nitrogen to which it is attached include 1-methyl-1-piperazinio, 1-methyl-1-piperidinio, 1-methyl-1-morpholinio, 1-methyl-1-pyrrolidinio, 1-methyl-1-hexamethyleneimino, 4-carbamoyl-1-methyl-1-piperidinio, 1-methyl-1,2,3,6-tetrahydropyridinio, etc. However, there is no suggestion in this patent that the R substituent may be the 2-aminothiazol-4-yl moiety or that the oximino substituent not contain a carboxyl group. United Kingdom Patent Specification No. 1,591,439 is concordant thereto and has a substantially identical disclosure.

COMPLETE DISCLOSURE

This application relates to novel cephalosporin derivatives which are potent antibacterial agents. More particularly, it relates to compounds of the formula

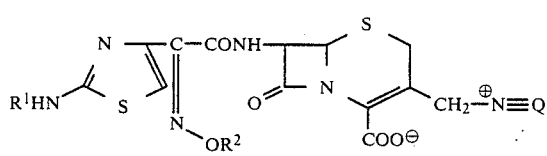

wherein $R^1$ is hydrogen or a conventional amino-protecting group, $R^2$ is a straight or branched chain alkyl, alkenyl or alkynyl group containing from 1 to 4 carbon atoms, and

is a quaternary ammonio group selected from

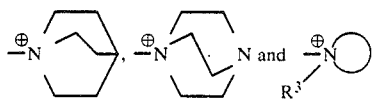

in which $R^3$ is (lower)alkyl, (lower)alkoxy(lower)alkyl, hydroxy(lower)alkyl with the provision that the hydroxy may not be on the α-carbon, carboxy(lower)alkyl, amino(lower)alkyl with the provision that the amino may not be on the α-carbon, (lower)alkenyl or halo(lower)alkyl, and

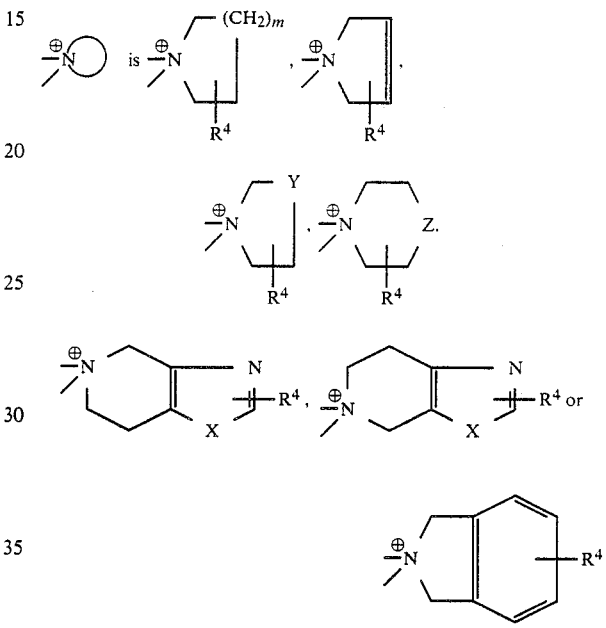

in which $R^4$ is hydrogen, hydroxy, halogen, (lower)alkyl, hydroxy(lower)alkyl, (lower)alkoxy(lower)alkyl, halo(lower)alkyl, amino(lower)alkyl, (lower)alkoxy, (lower)alkylthio, (lower)alkenyl, amino, (lower)alkylamino, di(lower)alkylamino, acylamino, acyloxy, carbamoyl, amidino(lower)alkyl, phenyl, pyridyl, amidino or guanidino, m is an integer of from 1 to 3, X is sulfur or —CH=CH—, Y is oxygen or sulfur, Z is oxygen, sulfur or N—$R^5$, and $R^5$ is hydrogen or (lower)alkyl, with the provision that

may not be the N-methylpyrrolidino moiety when $R^2$ is a $C_{1-4}$ alkyl or alkenyl group; and nontoxic, pharmaceutically acceptable salts and physiologically hydrolyzable esters thereof. Also included within the scope of the invention are the solvates (including hydrates) of the compounds of Formula I, as well as the tautomeric forms of the compounds of Formula I, e.g. the 2-iminothiazolin-4-yl form of the 2-aminothiazol-4-yl moiety.

As shown in the structural formula, the compounds of Formula I have the "syn" or "Z" configuration with respect to the alkoxyimino (or alkenyloxyimino or alkynyloxyimino) group. Because the compounds are geometric isomers, some of the "anti" isomer may also be present. This invention comprises compounds of Formula I containing at least 90% of the "syn" isomer. Preferably the compounds of Formula I are ∓syn"

isomers which are essentially free of the corresponding "anti" isomers.

The nontoxic pharmaceutically acceptable acid addition salts of the compounds of Formula I include the salts with hydrochloric, hydrobromic, formic, nitric, sulfuric, methanesulfonic, phosphoric, acetic, trifluoroacetic, fumaric, mandelic, ascorbic, malic and p-toluenesulfonic acids, and other acids which have been used in the penicillin and cephalosporin art.

Examples of physiologically hydrolyzable esters of the compounds of Formula I include indanyl, phthalidyl, methoxymethyl, acetoxymethyl, pivaloyloxymethyl, glycyloxymethyl, phenylglycyloxymethyl, and other physiologically hydrolyzable esters known and used in the penicillin and cephalosporin arts. Such esters are prepared by conventional techniques known in the art.

The compounds of Formula I in which $R^1$ is hydrogen exhibit high antibacterial activity against various Gram positive and Gram negative bacteria, and are useful in the treatment of bacterial infections in animals, including man. The compounds of Formula I may be formulated for parenteral use in a conventional manner utilizing known pharmaceutical carriers and excipients, and may be presented in unit dosage form or in multi-dosage containers. The compositions may be in the form of solutions, suspensions or emulsions in oily or aqueous vehicles, and may contain conventional dispersing, suspending or stabilizing agents. The compositions may also be in the form of a dry powder for reconstitution before use, e.g. with sterile, pyrogen-free water. The compounds of Formula I may also be formulated as suppositories utilizing conventional suppository bases such as cocoa butter or other glycerides. The compounds of this invention may, if desired, be administered in combination with other antibiotics such as penicillins or other cephalosporins.

When provided in unit dosage forms the compositions will preferably contain from about 50 to about 1500 mg of the active ingredient of Formula I. The dosage for adult human treatment will preferably be in the range of from about 500 to about 5000 mg per day, depending on the frequency and route of administration. When administered intramuscularly or intravenously to an adult human, a total dosage of from about 750 to about 3000 mg per day, in divided doses, normally will be sufficient, although higher daily doses of some of the compounds may be desirable in the case of Pseudomonas infections.

In another aspect, this invention relates to processes for the preparation of the compounds of Formula I. There are two basic procedures for converting a readily available starting cephalosporin to another cephalosporin having different substituents on the 7- and 3-positions. One may first remove the 7-substituent and replace it with the desired 7-substituent, and then insert the desired 3-substituent. Alternatively, one may first insert the desired 3-substituent and subsequently exchange the 7-substituent. The compounds of Formula I may be prepared by either procedure and both are included within the scope of this invention, but it is preferred to insert the desired 7-substituent first and then insert the desired 3-substituent. The preferred procedure is shown below in Reaction Scheme 1 while the alternative procedure is shown in Reaction Scheme 2. The abbreviation "Tr" represents the trityl (triphenylmethyl) group, which is a preferred amino-protecting group. The abbreviation "Ph" represents the phenyl group. Thus, the —CH(Ph)$_2$ moiety is the benzhydryl group, which is a preferred carboxyl-protecting group. In the reaction schemes, n may be 0 or 1.

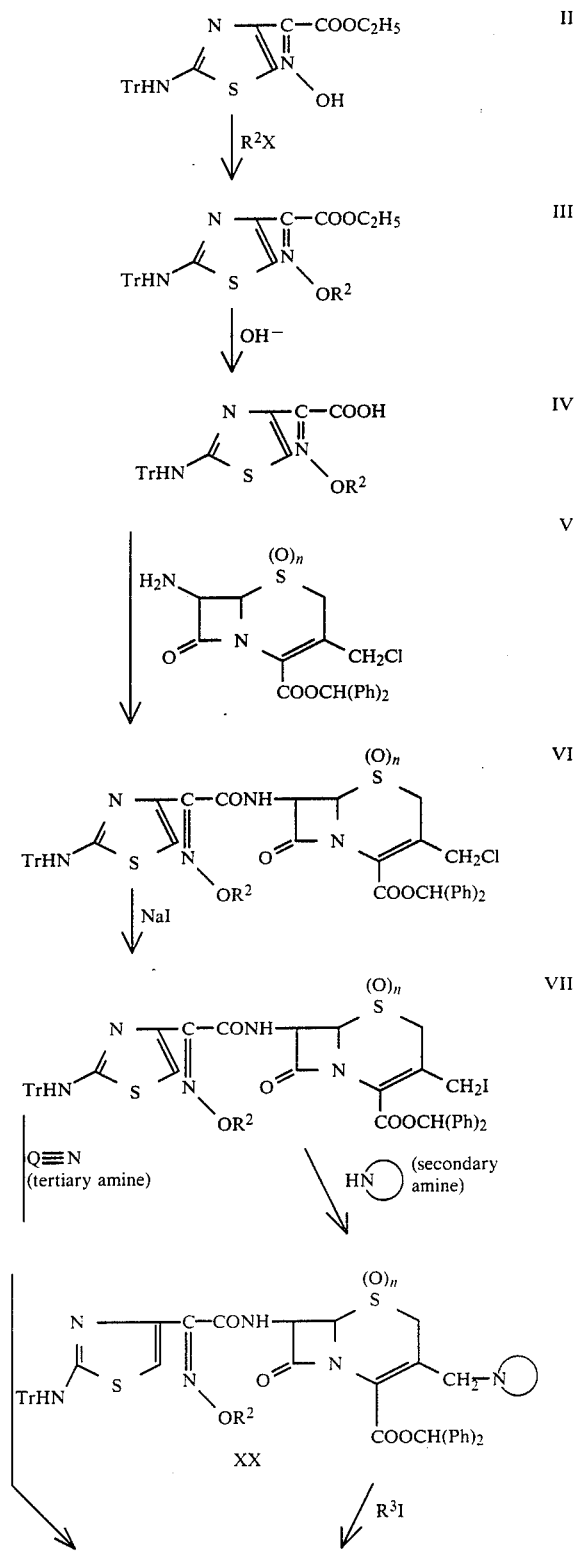

-continued

XXI

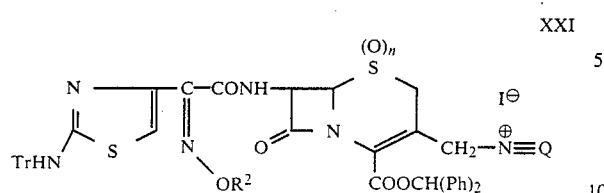

[reduction when n = 1]
deblock

I

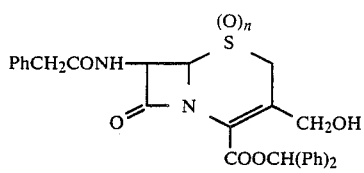

Reaction Scheme 2

VIII

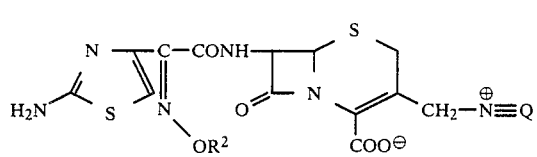

PCl$_5$
pyridine

IX

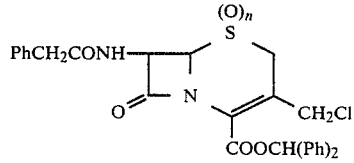

NaI

X

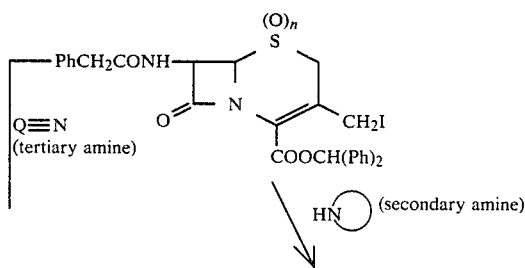

Q≡N (tertiary amine)

HN◯ (secondary amine)

XXII

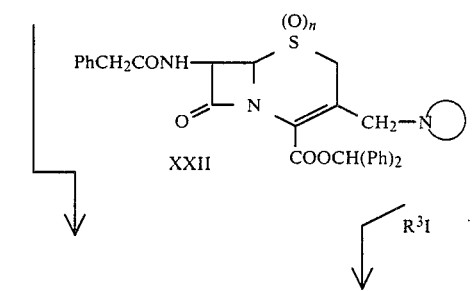

R$^3$I

-continued
Reaction Scheme 2

XI

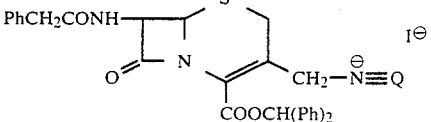

deacylation

XII

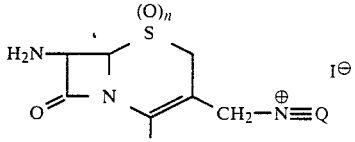

IV

XIII

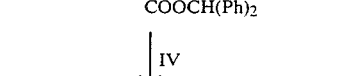

[reduction, when n = 1]
deblock

I

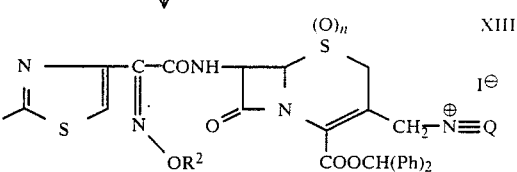

Reaction Scheme 1 shows alternate means of going from Compound VII to Compound XXI. The direct route, utilizing a tertiary amine (Q≡N) is applicable for the preparation of all compounds of Formula I. The indirect route, via Compound XX, uses a secondary amine as the initial reactant, and is quaternized in the following step. This indirect route is applicable only for the preparation of compounds of Formula I in which

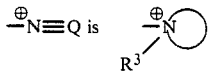

Similarly, in Reaction Scheme 2, the direct route from Compound X to Compound XI utilizes a tertiary amine (Q≡N) and is suitable for the preparation of all compounds of Formula I. The indirect route, via Compound XXII, is only suitable for the preparation of compounds of Formula I in which

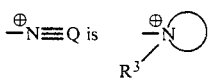

Although Reaction Scheme 1, above, shows a preferred mult-step procedure for the preparation of the compounds of Formula I, it will be appreciated that other starting materials and procedures may be utilized to prepare the intermediates used in the key step. Thus, the key step in Reaction Scheme 1 is the reaction of Compound VII with a tertiary amine to produce the "protected" product XXI (or the indirect reaction of Compound VII with a secondary amine, followed by quaternization to produce Compound XXI). The key Compound VII may, of course, be prepared by various other procedures. Similarly, the key step in Reaction Scheme 2 is the acylation of Compound XII with Compound IV. Both Compounds XII and IV may be prepared by other procedures.

The present invention provides a process for the preparation of compounds of the formula

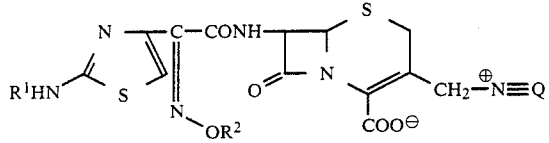
I wherein $R^1$ is hydrogen or a conventional amino-protecting group, $R^2$ is a straight or branched chain alkyl, alkenyl or alkynyl group containing from 1 to 4 carbon atoms, and

is a quaternary ammonio group selected from

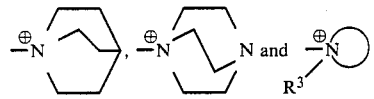

in which $R^3$ is (lower)alkyl, (lower)alkoxy(lower)alkyl, hydroxy(lower)alkyl with the provision that the hydroxy may not be on the α-carbon, carboxy(lower)alkyl, amino(lower)alkyl with the provision that the amino may not be on the α-carbon, (lower)alkenyl or halo(lower)alkyl, and

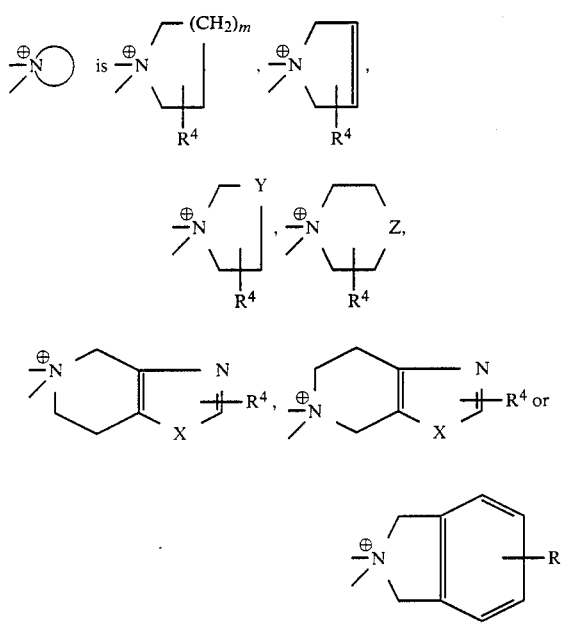

in which $R^4$ is hydrogen, hydroxy, halogen, (lower)alkyl, hydroxy(lower)alkyl, (lower)alkoxy(lower)alkyl, halo(lower)alkyl, amino(lower)alkyl, (lower)alkoxy, (lower)alkylthio, (lower)alkenyl, amino, (lower)alkylamino, di(lower)alkylamino, acylamino, acyloxy, carbamoyl, amidino(lower)alkyl, phenyl, pyridyl, amidino or guanidino, m is an integer of from 1 to 3, X is sulfur or —CH═CH—, Y is oxygen or sulfur, Z is oxygen, sulfur or N—$R^5$, and $R^5$ is hydrogen or (lower)alkyl, with the provision that

may not be the N-methylpyrrolidinio moiety when $R^2$ is a $C_{1-4}$ alkyl or alkenyl group, and nontoxic, pharmaceutically acceptable salts, physiologically hydrolyzable esters and solvates thereof, which comprises reacting a compound of the formula

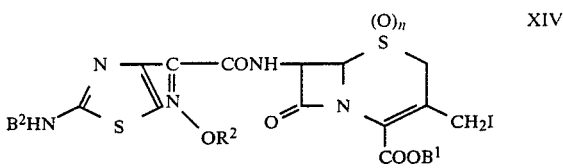
XIV in which $R^2$ is as defined above, n is 0 or 1, $B^1$ is a conventional carboxyl-protecting group and $B^2$ is a conventional amino-protecting group, with a tertiary amine Q≡N, as defined above, to produce a compound of the formula

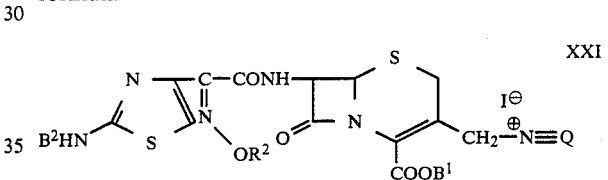
XXI and, if n is 1, reducing the sulfoxide by conventional means, and subsequently removing all protecting groups by conventional means.

The present invention also includes a process for the preparation of compounds of the formula

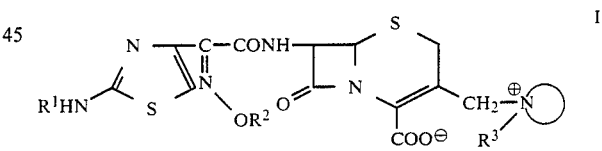
I wherein $R^1$ is hydrogen or a conventional amino-protecting group, $R^2$ is a straight or branched chain alkyl, alkenyl or alkynyl group containing from 1 to 4 carbon atoms, and

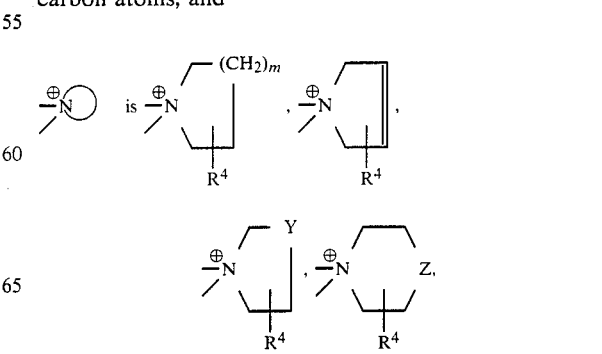

-continued

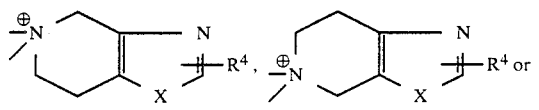

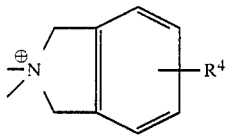

in which R⁴ is hydrogen, hydroxy, halogen, (lower)alkyl, hydroxy(lower)alkyl, (lower)alkoxy(lower)alkyl, halo(lower)alkyl, amino(lower)alkyl, (lower)alkoxy, (lower)alkylthio, (lower)alkenyl, amino, (lower)alkylamino, di(lower)alkylamino, acylamino, acyloxy, carbamoyl, amidino(lower)alkyl, phenyl, pyridyl, amidino or guanidino, m is an integer of from 1 to 3, X is sulfur or —CH=CH—, Y is oxygen or sulfur, Z is oxygen, sulfur or N—R⁵, and R⁵ is hydrogen or (lower)alkyl, with the provision that

may not be the N-methylpyrrolidinio moiety when R² is a C₁₋₄ alkyl or alkenyl group, and nontoxic, pharmaceutically acceptable salts, physiologically hydrolyzable esters and solvates thereof, which process comprises reacting a compound of the formula

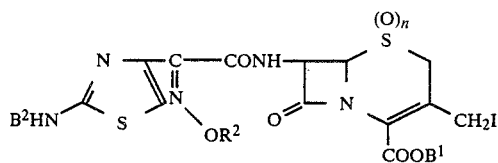

in which R² is as defined above, n is 0 or 1, B¹ is a conventional carboxyl-protecting group and B² is a conventional amino-protecting group, with a secondary amine of the formula

corresponding to the formula

as defined above, to produce a compound of the formula

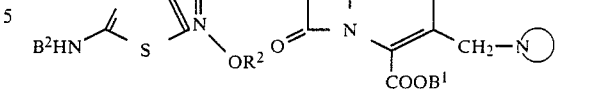

and further reacting said compound with a compound of the formula R³X, in which R³ is as defined above and X is halogen, to produce a compound of the formula

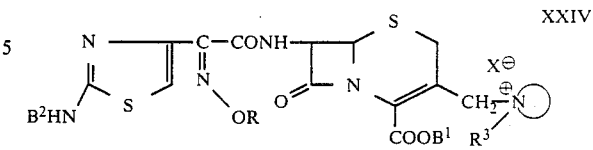

and, if n is 1, reducing the sulfoxide by conventional means, and subsequently removing all protecting groups by conventional means.

The reaction is carried out in a non-aqueous organic solvent such as methylene chloride, chloroform, ethyl ether, hexane, ethyl acetate, tetrahydrofuran, acetonitrile and the like, or mixtures of such solvents. The reaction is conveniently carried out at a temperature of from about −10° C. to about +50° C.; we normally prefer to conduct the reaction at room temperature. In Reaction Schemes 1 and 2, at least one mole of tertiary amine (or secondary amine) should be utilized per mole of Compound VII or X, respectively. We normally prefer to utilize from about 50% to about 100% excess of the amine. Similarly, at least one mole of Compound R³I should be utilized per mole of Compound XX or XXII, respectively.

Carboxyl-protecting groups suitable for use as B¹ in the above reaction are well-known to those skilled in the art and include aralkyl groups such as benzyl, p-methoxybenzyl, p-nitrobenzyl and diphenylmethyl (benzhydryl); alkyl groups such as t-butyl; haloalkyl groups such as 2,2,2-trichloroethyl, and other carboxyl-protecting groups described in the literature, e.g. in U.K. Pat. No. 1,399,086. We prefer to utilize carboxyl-protecting groups which are readily removed by treatment with acid. Particularly preferred carboxyl-protecting groups are the benzhydryl and t-butyl moieties.

Amino-protecting groups suitable for use as B² are also well-known in the art, and include the trityl group and acyl groups such as chloroacetyl, formyl and trichloroethoxycarbonyl. Amino-protecting groups which are readily removed by treatment with acid, e.g. the trityl group, are preferred.

When the cephalosporin nucleus is utilized in the form of the 1-oxide (n=1), the 1-oxide is prepared by known procedures such as oxidation with m-chloroperbenzoic acid, peracetic acid, etc. The 1-oxide subsequently may be reduced by known procedures, e.g. reduction of the corresponding alkoxysulfonium salt with iodide ion in an aqueous medium. The alkoxysulfonium salt itself is readily prepared by treatment of the 1-oxide with, for example, acetyl chloride.

The acylating derivatives of the acid of Formula IV include the acid halides (and particularly the acid chloride), mixed acid anhydrides (such as the acid anhydrides formed with pivalic acid or a haloformate such as ethyl chloroformate), and activated esters (such as may be formed with N-hydroxybenztriazole in the presence of a condensing agent such as dicyclohexylcarbodiimide). The acylation may also be effected by use of the free acid of Formula IV in the presence of a condensing agent such as dicyclohexylcarbodiimide, carbonyldiimidazole or an isoxazolium salt. The preferred acylating derivative of the acid of Formula IV is the acid chloride, preferably used in the presence of an acid binding agent (and particularly a tertiary amine acid binding agent such as triethylamine, dimethylaniline or pyridine).

When the acylation is conducted with an acid halide it is possible to utilize an aqueous reaction medium, but a non-aqueous medium is preferred. When acid anhydrides, activated esters, or the free acid in the presence of a condensing agent, are used for the acylation, the reaction medium should be non-aqueous. Particularly preferred solvents for the acylation reaction are halogenated hydrocarbons such as methylene chloride and chloroform, but tertiary amides such as dimethylacetamide or dimethylformamide may be utilized, as well as other conventional solvents such as tetrahydrofuran, acetonitrile and the like.

The acylation reaction may be conducted at a temperature of from about −50° C. to about +50° C. However, it is preferably conducted at or below room temperature and most preferably from about −30° C. to about 0° C. It is usually preferred to acylate the compound of Formula V or XII with about a stoichiometric amount of the acylating agent of Formula IV, although a small excess (e.g. 5–25%) of the acylating agent may be utilized.

It sometimes is preferable that the compound of Formula V or XII be acylated in the form of its N-silyl derivative (when utilizing a non-aqueous reaction medium). This is conveniently done in situ by simply adding a suitable silylating agent (e.g. N,O-bistrimethylsilylacetamide) to the solution of Compound V or XII prior to the addition of the acylating agent of Formula IV. We prefer to utilize about 3 moles of silylating agent per mole of Compound V or XII although this is not critical. The silyl compound is readily removed after acylation by the addition of water.

Preferred compounds of Formula I are those in which $R^2$ is methyl. More preferred compounds are those in which $R^2$ is methyl and

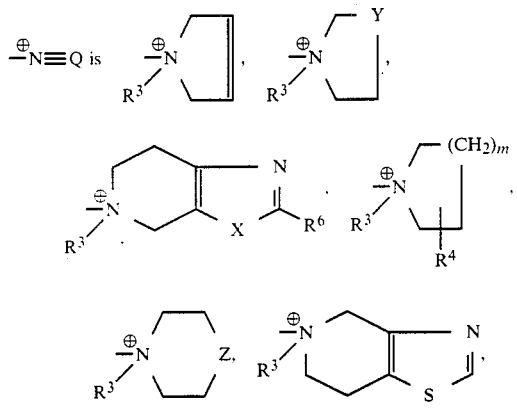

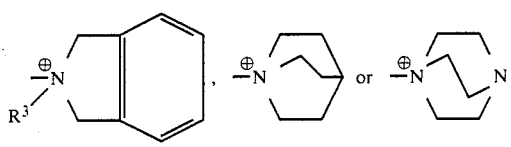

in which X is sulfur or —CH=CH—, Y is oxygen or sulfur, m is 1, 2 or 3, Z is oxygen, sulfur or N—$R^5$, $R^5$ is hydrogen or methyl, $R^6$ is hydrogen or amino, $R^3$ is methyl, ethyl, 2-hydroxyethyl, carboxymethyl or allyl, and $R^4$ is hydrogen, methyl, hydroxy or carbamoyl, provided that $R^3$ may not be methyl when m is 1 and $R^4$ is hydrogen.

Particularly preferred compounds are:
(1) 7-[(Z)-2-(2-aminothiazol-4-yl)-2-methoxyiminoacetamido]-3-(1-methyl-1-piperidinio)methyl-3-cephem-4-carboxylate,
(2) 7-[(Z)-2-(2-aminothiazol-4-yl)-2-methoxyiminoacetamido]-3-(4-methyl-4-morpholinio)methyl-3-cephem-4-carboxylate,
(3) 7-[(Z)-2-(2-aminothiazol-4-yl)-2-methoxyiminoacetamido]-3-(1-quinuclidinio)methyl-3-cephem-4-carboxylate,
(4) 7-[(Z)-2-(2-aminothiazol-4-yl)-2-methoxyiminoacetamido]-3-(1,4-diazabicyclo[2,2,2]octan-1-io)methyl-3-cephem-4-carboxylate,
(5) 7-[(Z)-2-(2-aminothiazol-4-yl)-2-methoxyiminoacetamido]-3-(1,4-dimethyl-1-piperazinio)-methyl-3-cephem-4-carboxylate,
(6) 7-[(Z)-2-(2-aminothiazol-4-yl)-2-methoxyiminoacetamido]-3-(5-methyl-4,5,6,7-tetrahydro-5-thiazolo[4,5-c]pyridinio)methyl-3-cephem-4-carboxylate,
(7) 7-[(Z)-2-(2-aminothiazol-4-yl)-2-methoxyiminoacetamido]-3-(1-methylhexahydroazepinio)-methyl-3-cephem-4-carboxylate,
(8) 7-[(Z)-2-(2-aminothiazol-4-yl)-2-methoxyiminoacetamido]-3-[(S)-2-carbamoyl-1-methylpyrrolidinio]methyl-3-cephem-4-carboxylate,
(9) 7-[(Z)-2-(2-aminothiazol-4-yl)-2-methoxyiminoacetamido]-3-(3-hydroxy-1-methylpyrrolidinio)methyl-3-cephem-4-carboxylate,
(10) 7-[(Z)-2-(2-aminothiazol-4-yl)-2-methoxyiminoacetamido]-3-(1-ethylpyrrolidinio)methyl-3-cephem-4-carboxylate,
(11) 7-[(Z)-2-(2-aminothiazol-4-yl)-2-methoxyiminoacetamido]-3-(1-methyl-3-pyrrolinio)methyl-3-cephem-4-carboxylate,
(12) 7-[(Z)-2-(2-aminothiazol-4-yl)-2-methoxyiminoacetamido]-3-(3-methyloxazolidinio)methyl-3-cephem-4-carboxylate,
(13) 7-[(Z)-2-(2-aminothiazol-4-yl)-2-methoxyiminoacetamido]-3-(3-methylthiazolidinio)methyl-3-cephem-4-carboxylate,
(14) 7-[(Z)-2-(2-aminothiazol-4-yl)-2-methoxyiminoacetamido]-3-(2-methyl-2-benzo[c]pyrrolinio)-methyl-3-cephem-4-carboxylate,
(15) 7-[(Z)-2-(2-aminothiazol-4-yl)-2-methoxyiminoacetamido]-3-(2-amino-6-methyl-4,5,6,7-tetrahydro-6-thiazolo[5,4-c]pyridinio)methyl-3-cephem-4-carboxylate,
(16) 7-[(Z)-2-(2-aminothiazol-4-yl)-2-methoxyiminoacetamido]-3-[1-(carboxymethyl)pyrrolidinio]methyl-3-cephem-4-carboxylate,

(17) 7-[(Z)-2-(2-aminothiazol-4-yl)-2-methoxyiminoacetamido]-3-[(1-hydroxyethyl)pyrrolidinio]methyl-3-cephem-4-carboxylate,

(18) 7-[(Z)-2-(2-aminothiazol-4-yl)-2-propargyloxyiminoacetamido]-3-(1-methylpyrrolidinio)methyl-3-cephem-4-carboxylate,

(19) 7-[(Z)-2-(2-aminothiazol-4-yl)-2-methoxyiminoacetamido]-3-(1,2-dimethylpyrrolidinio)methyl-3-cephem-4-carboxylate,

(20) 7-[(Z)-2-(2-aminothiazol-4-yl)-2-methoxyiminoacetamido]-3-(4-methylthiomorpholinio)methyl-3-cephem-4-carboxylate,

(21) 7-[(Z)-2-(2-aminothiazol-4-yl)-2-methoxyiminoacetamido]-3-(1-allylpyrrolidinio)methyl-3-cephem-4-carboxylate,

(22) 7-[(Z)-2-(2-aminothiazol-4-yl)-2-ethoxyiminoacetamido]-3-(1-methylpiperidinio)methyl-3-cephem-4-carboxylate,

(23) 7-[(Z)-2-(2-aminothiazol-4-yl)-2-methoxyiminoacetamido]-3-(6-methyl-5,6,7,8-tetrahydro-6-[1,6]naphthylidinio)methyl-3-cephem-4-carboxylate and

(24) 7-[(Z)-2-(2-aminothiazol-4-yl)-2-allyloxyiminoacetamido]-3-(1-methylpiperidinio)methyl-3-cephem-4-carboxylate.

As used herein, the terms acylamino and acyloxy refer to an acylated amino or acylated hydroxy group in which the acyl moiety is (lower)alkanoyl (e.g. formyl, acetyl, propionyl, butyryl, isobutyryl, isovaleryl, etc.), aroyl (e.g. benzoyl, etc.), (lower)alkanesulfonyl (e.g. mesyl, ethanesulfonyl, etc.) or arylsulfonyl (e.g. benzenesulfonyl, tosyl, etc.).

As used herein, the terms "(lower)alkyl", "(lower)alkoxy", "(lower)alkylthio" (or the like) mean straight or branched chain alkyl, alkoxy, alkylthio (or the like) groups containing from 1 to 6 carbon atoms, inclusive.

In the primary evaluation of the compounds of this invention, the Minimum Inhibitory Concentrations (MIC's) of the compounds were determined by the two-fold serial agar dilution method in Mueller-Hinton agar against 32 strains of test organisms in six groups. The geometric means of the MIC's determined in these tests are shown in Table 1.

TABLE 1

| | Minimum Inhibitory Concentrations (mcg/ml) | | | | | |
|---|---|---|---|---|---|---|
| | Geometric Mean of MIC (mcg/ml) | | | | | |
| Compound of Example | Gp-Ia (5 strains) | Gp-Ib (5) | Gn-Ia (5) | Gn-Ib (5) | Gn-II (5) | Gn-III (7) |
| 1 | 1.3 | 2.9 | 0.030 | 0.14 | 0.55 | 3.2 |
| 2 | 1.7 | 5.0 | 0.061 | 0.22 | 0.96 | 4.0 |
| 3 | 0.77 | 2.5 | 0.040 | 0.14 | 0.84 | 2.8 |
| 4 | 2.9 | 5.8 | 0.070 | 0.16 | 0.80 | 3.6 |
| 5 | 2.3 | 4.7 | 0.057 | 0.12 | 0.78 | 3.6 |
| 6 | 0.9 | 3.2 | 0.025 | 0.15 | 0.40 | 4.2 |
| 7 | 0.9 | 3.2 | 0.05 | 0.13 | 0.15 | 4.2 |
| 8 Isomer A | 2.1 | 4.7 | 0.098 | 0.39 | 0.35 | 11 |
| 8 Isomer B | 1.6 | 4.1 | 0.057 | 0.20 | 0.23 | 7.2 |
| 9 | 1.3 | 3.3 | 0.27 | 0.14 | 0.14 | 2.9 |
| 10 | 1.0 | 2.0 | 0.037 | 0.13 | 0.13 | 3.1 |
| 11 | 0.78 | 2.1 | 0.019 | 0.17 | 0.15 | 2.5 |
| 12 Isomer A | 1.1 | 4.4 | 0.046 | 0.25 | 0.21 | 5.4 |
| 12 Isomer B | 1.3 | 4.4 | 0.040 | 0.21 | 0.18 | 4.0 |
| 13 Isomer A | 0.84 | 3.1 | 0.046 | 0.28 | 0.28 | 5.9 |
| 13 Isomer B | 0.72 | 1.6 | 0.029 | 0.13 | 0.13 | 2.5 |
| 14 | 0.51 | 1.7 | 0.042 | 0.13 | 0.13 | 7.7 |
| 15 | 1.1 | 2.8 | 0.034 | 0.16 | 0.18 | 4.6 |
| 16 | 6.5 | 17 | 0.020 | 0.23 | 0.14 | 5.1 |
| 17 | 1.6 | 4.1 | 0.057 | 0.15 | 0.20 | 4.1 |
| 18 | 0.77 | 2.2 | 0.061 | 0.32 | 0.36 | 4.0 |
| 19 | 1.4 | 3.8 | 0.078 | 0.27 | 0.27 | 6.0 |

TABLE 1-continued

| | Minimum Inhibitory Concentrations (mcg/ml) | | | | | |
|---|---|---|---|---|---|---|
| | Geometric Mean of MIC (mcg/ml) | | | | | |
| Compound of Example | Gp-Ia (5 strains) | Gp-Ib (5) | Gn-Ia (5) | Gn-Ib (5) | Gn-II (5) | Gn-III (7) |
| 20 | 1.2 | 4.1 | 0.064 | 0.25 | 0.25 | 3.7 |
| 21 | 1.1 | 2.9 | 0.045 | 0.15 | 0.18 | 6.5 |
| 22 Isomer A | 1.2 | 4.2 | 0.044 | 0.20 | 0.15 | 5.0 |
| 22 Isomer B | 1.6 | 4.1 | 0.049 | 0.17 | 0.17 | 7.2 |
| 23 | 1.4 | 2.9 | 0.070 | 0.28 | 0.96 | 6.3 |

Gp-Ia: Penicillin(PC)-sensitive S. aureus
Gp-Ib: PC-resistant S. aureus
Gn-Ia: Cephalothin(CET)-sensitive E. coli (2 strains), K. pneumoniae (1) and P. mirabilis (2)
Gn-Ib: CET-resistant E. coli (3) and K. pneumoniae (2)
Gn-II: M. morganii (1), E. cloacae (2) and S. marcescens (2)
Gn-III: P. aeruginosa

PREPARATION NO. 1

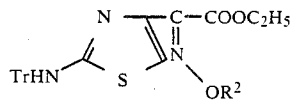

Ethyl (Z)-2-Methoxyimino-2-(2-tritylaminothiazol-4-yl)acetate (IIIa)

A mixture of ethyl (Z)-2-hydroxyimino-2-(2-tritylaminothiazol-4-yl)acetate (II) (5.00 g, 10.9 mmoles), CH$_3$I (2.04 ml, 32.8 mmoles) and K$_2$CO$_3$ (4.54 g, 32.8 mmoles) in dry dimethylsulfoxide (DMSO) (100 ml) was stirred at room temperature overnight and then poured into water (250 ml). The precipitate which formed was collected by filtration, washed with water and dried to give the title compound (5.15 g, quantitative yield). Mp. 115° C. (dec.)

NMR: $\delta^{CDCl_3}$ ppm 1.32 (3H, t), 3.98 (3H, s), 4.30 (2H, q), 6.42 (1H, s), 7.2 (1H, m), 7.25 (15H, s).

Compounds IIIb, IIIc, IIId and IIIe were prepared by the general procedure set forth above, but replacing the methyl iodide with the appropriate iodide.

| Compound | R$^2$ | Yield (%) | Mp (°C.) | Literature Mp (°C.) |
|---|---|---|---|---|
| IIIa | methyl | 100 | 115° (dec.) | 120° (dec.)[1] |
| IIIb | ethyl | 67 | 97-98° | *[1] |
| IIIc | isopropyl | 26 | 52-55° | *[1] |
| IIId | allyl | * | * | *[1] |
| IIIe | propargyl | 94 | 70-73 | *[2] |

*The ester was hydrolyzed without isolation
[1]Tetrahedron, 34, 2233 (1978)
[2]U.S. Pat. No. 4,294,960

PREPARATION NO. 2

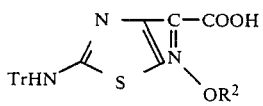

(Z)-2-Methoxyimino-2-(2-tritylaminothiazol-4-yl)acetic acid (IVa)

The ethyl ester IIIa prepared in Preparation No. 1 (6.00 g, 12.7 mmoles) in ethanol (120 ml) was treated with 2N NaOH (12.7 ml) at room temperature overnight. The reaction mixture was adjusted to pH 8 by the addition of powdered dry ice and the solvent was evaporated under reduced pressure. The residue was dissolved in water (100 ml) and the solution was acidified with 1N HCl to pH 2 and then extracted with ethyl acetate (3×50 ml). The combined extracts were washed with a saturated aqueous NaCl solution, dried and evaporated. The residue was crystallized from ethyl acetate-hexane to afford 5.56 g (yield 98%) of the title product. Mp. 138°–143° C. (dec.).

NMR: $\delta^{CDCl_3}$ ppm 3.89 (3H, s), 6.52 (1H, s), 7.2 (15H, s).

Compounds IVb, IVc, IVd and IVe were prepared by the general procedure set forth above.

| Compound | R² | Yield (%) | Mp (°C., dec.) | Literature Mp (°C., dec.) |
|---|---|---|---|---|
| IVa | methyl | 98 | 138–143 | ca. 140[1] |
| IVb | ethyl | 85 | 140–145 | not reported[1] |
| IVc | isopropyl | 85 | 166–169 | ca. 170[1] |
| IVd | allyl | 66 | 170–178 | ca. 170[1] |
| IVe | propargyl | 88 | 136–138 | not reported[2] |

[1]Tetrahedron, 34, 2233 (1978)
[2]The corresponding NH₂ compound is described in U.S. Pat. No. 4,294,960

PREPARATION NO. 3

Benzhydryl 3-Hydroxymethyl-7-phenylacetamido-3-cephem-4-carboxylate (VIII)

To a stirred suspension of phosphate buffer (pH 7, 162.5 ml) and wheat bran (20 g, dry) at room temperature was added 7-phenylacetamidocephalosporanic acid sodium salt (5 gm, 12.1 mmoles) in one portion. The progress of the reaction was monitored by HPLC until the hydrolysis was complete (5 hours). The suspension was filtered to remove the wheat bran and the filtrate was cooled to 5°–10° C. for extractive esterification. To the cooled solution was added methylene chloride (32 ml) followed by a 0.5M solution of diphenyldiazomethane in methylene chloride (24 ml). The pH was then adjusted to 3.0 with 28% phosphoric acid. After 1 hour the reaction mixture was allowed to rise to 20° C. Heptane (56 ml) was slowly added and the resulting crystalline title product was recovered by filtration. Yield of the title product was 3.0 gm (50%).

PREPARATION NO. 4

Benzhydryl 7-Amino-3-chloromethyl-3-cephem-4-carboxylate (V)

To a slurry of PCl₅ (8.3 g, 40 mmoles) in CH₂Cl₂ (100 ml) was added pyridine (3.2 g, 40 mmoles) and the mixture was stirred for 20 minutes at 20° C. To the mixture was added benzhydryl 3-hydroxymethyl-7-phenylacetamido-3-cephem-4-carboxylate prepared in Preparation No. 3 (5.1 g, 10 mmoles) with stirring at −40° C., in one portion. The mixture was stirred at −10° C. for 15 minutes and allowed to stand at −10° C. to −15° C. for 7 hours. To the cooled solution (−20° C.) was added propane-1,3-diol (10 ml) and the mixture was allowed to stand at −20° C. for 16 hours and then at room temperature for 20 minutes with stirring. The resulting solution was washed with ice-water (2×20 ml) and saturated aqueous NaCl (10 ml), dried over MgSO₄ and concentrated in vacuo. The gummy residue (12 g) was dissolved in a mixture of CHCl₃ and n-hexane (2:1), and subjected to chromatography using a silica gel column (200 g) and the same solvent as eluant. Fractions containing the title compound were evaporated in vacuo and the residue triturated with n-hexane to give the title product (2.1 g, 51%), melting at >110° C. (dec.).

IR: $\nu_{KBr}$ 3400, 2800, 1785, 1725 cm⁻¹.
UV: $\lambda_{max}^{EtOH}$ 625 nm (E₁ $_{cm}^{1\%}$ 160).
NMR: $\delta_{ppm}^{DMSO-d_6+CDCl_3}$ 3.69 (2H, s), 4.43 (2H, s), 5.09 (1H, d, J=4.5 Hz), 5.24 (1H, d, J=4.5 Hz), 6.87 (1H, s), 7.3 (10H, m).

PREPARATION NO. 5

Benzhydryl 3-Chloromethyl-7-[(Z)-2-methoxyimino-2-(2-tritylaminothiazol-4-yl)acetamido]-3-cephem-4-carboxylate (VIa)

Benzhydryl 7-amino-3-chloromethyl-3-cephem-4-carboxylate (V) prepared in Preparation No. 4 (2.29 g, 5.52 mmoles) in CH₃CN (57 ml) was treated with bis(-trimethylsilyl)acetamide (BSA, 4.09 ml, 16.6 mmoles) at room temperature for 50 minutes to give a clear solution. To the solution was added an acid chloride solution, which was prepared from (Z)-2-methoxyimino-2-(2-tritylaminothiazol-4-yl)acetic acid (IV-a) (2.04 g, 4.60 mmoles) and PCl₅ (1.15 g, 5.52 mmoles) in methylene chloride (20 ml). The mixture was stirred at room temperature for 30 minutes, poured into cold water (200 ml) and extracted with ethyl acetate (3×100 ml). The combined extracts were washed with aqueous NaCl, dried and evaporated. The residual syrup (4 g) was chromatographed on a silica gel (150 g) column by eluting with 10:1 and 3:1 mixtures of toluene and ethyl acetate successively. The fractions containing the desired compound were combined and evaporated to afford 2.61 g (68%) of VIa as an amorphous powder.

NMR: $\delta^{CDCl_3}$ ppm 3.50 (2H, s), 4.02 (3H, s), 4.33 (2H, s), 4.98 (1H, d), 5.87 (1H, q), 6.65 (1H, s), 6.90 (1H, s), 7.3 (25H, m).

PREPARATION NO. 6

Benzhydryl 3-Iodomethyl-7-[(Z)-2-methoxyimino-2-(2-tritylaminothiazol-4-yl)acetamido]-3-cephem-4-carboxylate (VIIa)

A mixture of the 3-chloromethyl derivative prepared in Preparation No. 5 (VIa) (1.50 g, 1.79 mmoles) and NaI (1.34 g, 8.93 mmoles) in methyl ethyl ketone (30 ml) was stirred at room temperature for 1 hour. After evaporation of the solvent the residue was dissolved in ethyl acetate (100 ml) and washed with water, aqueous Na₂S₂O₃ and aqueous NaCl, dried and evaporated to give the title compound VIIa (1.47 g, 89%) as an amorphous powder.

NMR: $\delta^{CDCl_3}$ ppm 3.55 (2H, ABq), 4.00 (3H, s), 4.25 (2H, s), 4.97 (1H, d), 5.80 (1H, q), 6.65 (1H, s), 6.90 (1H, s), 7.3 (25H, m).

PREPARATION NO. 7

Benzhydryl 3-Chloromethyl-7-[(Z)-2-ethoxyimino-2-(2-tritylaminothiazol-4-yl)acetamido]-3-cephem-4-carboxylate (VIb)

To a solution of (Z)-2-ethoxyimino-2-(2-tritylaminothiazol-4-yl)acetic acid (IVb) (1.095 g, 2.4 mmoles) in dichloromethane (20 mL) was added phosphorus pentachloride (500 mg). After stirring for 1 hour at room temperature, the mixture was added in one portion to an ice-cooled solution of Compound V (1.083 g, 2.4 mmoles) and BSA (1 ml) in dichloromethane (20 ml).

After stirring for 0.5 hour the reaction mixture was poured into 10% aqueous NaHCO₃ (200 ml) and extracted with CHCl₃ (100 ml). The extract was washed with water, dried over MgSO₄, and evaporated under reduced pressure. The residue was chromatographed on a silica gel column. Elution with CHCl₃ gave VIb as an amorphous powder, 1.76 g (86%).

NMR: $\delta^{CDCl_3}$ ppm 1.40 (3H, t, CH₂CH₃), 3.53 (2H, ABq, 2-H), 4.37 (2H, s, —CH₂Cl), 4.60 (2H, q, —CH₂CH₃), 4.90 (1H, d, 6-H), 5.89 (1H, d, 7-H), 6.88 (1H, s, thiazole-H), 6.91 (1H, s, benzhydryl-CH).

PREPARATION NO. 8

Diphenylmethyl 7-[(Z)-2-Ethoxyimino-2-(2-tritylaminothiazol-4-yl)acetamido]-3-iodomethyl-3-cephem-4-carboxylate (VIIb)

A mixture of VIb prepared in Preparation No. 7 (1.07 g, 1.25 mmoles) and NaI (562 mg, 2.75 mmoles) in acetone (20 ml) was stirred for 1 hour. The mixture was filtered and the filtrate was poured into water and extracted with ethyl acetate. The organic layer was washed successively with 5% aqueous Na₂S₂O₃, water and saturated aqueous NaCl, dried over MgSO₄ and evaporated to give 1.04 g (89%) of Compound VIIb.

NMR: $\delta^{CDCl_3}$ ppm 3.55 (2H, q, 2-H), 4.27 (2H, s, CH₂I), 5.02 (1H, d, 6-H), 5.87 (1H, d, 7-H), 6.68 (1H, s, thiazole ring H), 6.93 (1H, s, benzhydryl-CH).

PREPARATION NO. 9

Benzhydryl 3-Chloromethyl-7-phenylacetamido-3-cephem-4-carboxylate (IX)

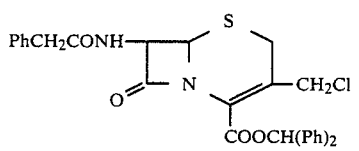

Pyridine (1.6 g, 20 mmole) was added to a slurry of PCl₅ (4.2 g, 20 mmole) in CH₂Cl₂ (100 ml) and the mixture was stirred at 20° C. for 20 minutes and then cooled to −40° C. To the mixture was added benzhydryl 3-hydroxymethyl-7-phenylacetamido-3-cephem-4-carboxylate (VIII) (5.1 g, 10 mmole) in one portion. The mixture was stirred at −10° C. for 30 minutes. The solution was washed with iced water (20 ml) and poured into iced saturated aqueous NaHCO₃ (100 ml), with stirring. The CH₂Cl₂ layer was washed successively with saturated aqueous NaCl (50 ml), 10% HCl (50 ml) and saturated aqueous NaCl. The dried CH₂Cl₂ solution was evaporated and the residue triturated with n-hexane to give 5.2 g (98%) of IX. Mp. 85° C. (dec.).

ir: $\nu_{KBr}$ 3250, 1780, 1720, 1660 cm⁻¹.

uv: $\lambda_{EtOH}^{max}$ 265 nm (E₁ ₖₘ 1% 140).

nmr: $\delta_{ppm}^{DMSO-d_6}$ 3.53 (2H, s), 3.62 (2H, broad s), 4.39 (2H, s), 5.13 (2H, d, J=4.5), 5.75 (1H, d-d, J=4.5, 9), 6.93 (1H, s), 7.1–7.6 (15H, m), 9.12 (1H, d, J=9).

Analysis Calc'd. for C₂₉H₂₅N₂O₄SCl.½H₂O: C, 64.26; H, 4.83; N, 5.17; S, 5.92. Found: C, 64.53; H, 5.15; N, 4.78; S, 5.92.

PREPARATION NO. 10

Benzhydryl 3-Iodomethyl-7-phenylacetamido-3-cephem-4-carboxylate (X)

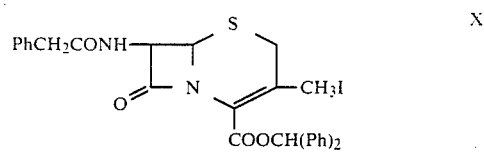

A solution of Compound IX from Preparation No. 9 (1.07 g, 2 mmoles) in acetone (10 ml) containing NaI (900 mg, 6 mmoles) was stirred for 2 hours at ambient temperature. The reaction mixture was evaporated under reduced pressure and the residue was partitioned between CH₂Cl₂ (30 ml) and water (10 ml). The lower layer was washed with 10% w/v aqueous sodium thiosulfate (10 ml) and saturated aqueous NaCl (10 ml), dried over MgSO₄ and evaporated to dryness to give 1.1 g (88%) of X as a reddish amorphous powder melting at 75° C. (dec.).

ir: $\nu_{KBr}$ 3300, 1780, 1720, 1660 cm⁻¹.

uv: $\lambda_{max}^{EtOH}$ 280 nm (E₁ ₖₘ 1% 100).

PREPARATION NO. 11

Benzhydryl 3-Chloromethyl-7-phenylacetamido-3-cephem-4-carboxylate 1-Oxide (IX-oxide)

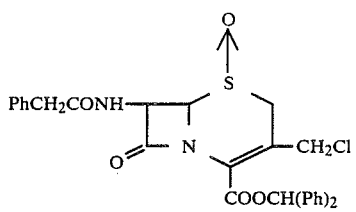

A mixture of IX (1.5 g, 2.8 mmole) and 3-chloroperbenzoic acid (970 mg, 5.6 mmole) in CH₃OH:CH₂Cl₂ (3:7) (50 ml) was stirred for 3 hours at room temperature and then evaporated to dryness. The residue was triturated with ether (50 ml) to separate 1.1 g (71%) of IX-oxide as a colorless amorphous powder. Mp. 196° C.–199° C. (dec.).

ir: $\nu_{KBr}$ 3300, 1780, 1660, 1620, 1030 cm⁻¹.

uv: $\lambda_{max}^{EtOH}$ 272 nm (E₁ ₖₘ 1% ca. 140).

nmr: $\delta_{ppm}^{DMSO-d_6}$ 3.69 & 3.71 (2H, each s), 3.68 & 3.99 (each 1H, d, J=15), 4.38 & 4.62 (each 1H, d, J=12), 4.96 (1H, d, J=4.5), 5.85 (1H, d-d, J=4.5, 7.5), 6.90 (1H, s), 7.1–7.5 (15H, m), 8.40 (1H, d, J=7.5).

Analysis Calc'd. for C₂₉H₂₅N₂O₅SCl: C, 63.44; H, 4.59; N, 5.10; S, 5.84. Found: C, 63.35; H, 4.51; N, 4.81; S, 6.02.

PREPARATION NO. 12

Benzhydryl 3-Iodomethyl-7-phenylacetamido-3-cephem-4-carboxylate 1-Oxide (X-oxide)

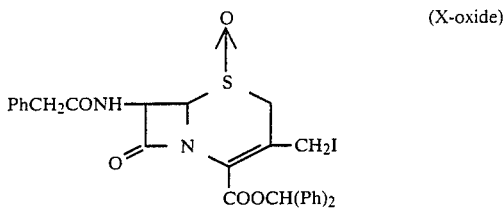

(X-oxide)

A mixture of IX-oxide (1 g, 1.8 mmole) and NaI (810 mg, 5.4 mmole) in acetone (10 ml) was stirred for 3 hours at ambient temperature and then evaporated in vacuo. The residual oil was partitioned between 10% $CH_3OH$ in $CH_2Cl_2$ (50 ml) and water (10 ml). The organic solvent layer was washed with 10% w/v aqueous sodium thiosulfate (10 ml) and saturated aqueous NaCl, dried over $MgSO_4$ and then evaporated to dryness to give 1.1 g (94%) of X-oxide melting at 144° C. (dec.).

ir: $\nu_{KBr}$ 3300, 1790, 1710, 1650, 1030 cm$^{-1}$.

uv: $\lambda_{max}{}^{EtOH}$ 291 nm (E$_1$ $_{cm}$$^{1\%}$ ca. 140).

nmr: $\delta_{ppm}{}^{DMSO-d6}$ 3.58 & 3.60 (2H, each s), 3.84 (2H, broad s), 4.25 & 4.99 (each 1H, d, J=9), 4.90 (1H, d, J=4.5), 5.80 (1H, d-d, J=4.5 & 7.5), 6.91 (1H, s), 7.1–7.6 (15H, m), 8.35 (1H, d).

PREPARATION NO. 13

Diphenylmethyl 3-Chloromethyl-7-[(Z)-2-(2-propoxyimino)-2-(2-tritylaminothiazol-4-yl)acetamido]-3-cephem-4-carboxylate (VIc)

A mixture of (Z)-2-(2-propoxyimino)-2-(2-tritylaminothiazol-4-yl)acetic acid (IVc) (707 mg, 1.5 mmoles) and phosphorus pentachloride (344 mg, 1.65 mmoles) in dichloromethane (14 ml) was stirred at room temperature for 1 hour and poured into a solution of Compound V (677 mg, 1.5 mmoles) and BSA (1.1 ml, 4.5 mmoles) in dichloromethane (15 ml). The reaction mixture was stirred at room temperature for 30 minutes, diluted with ethyl acetate (200 ml), washed with aqueous sodium bicarbonate (100 ml) and water (3×100 ml), dried over sodium sulfate and evaporated to give 1.4 g (100%) of Compound VIc.

IR: $\nu_{max}{}^{KBr}$ cm$^{-1}$ 3360, 3020, 3060, 2960, 1785, 1725, 1680, 1520, 1500, 1450, 1375, 1300, 1250, 1160, 1090, 1060, 1010, 990, 900, 840, 750, 700.

UV: $\lambda_{max}{}^{EtOH}$ nm(ε) 240 (24600), 260 (20700).

PREPARATION NO. 14

Diphenylmethyl 3-Iodomethyl-7-[(Z)-2-(2-propoxyimino)-2-(2-tritylaminothiazol-4-yl)acetamido]-3-cephem-4-carboxylate (VIIc)

A mixture of Compound VIc (500 mg, 0.55 mmole) and sodium iodide (248 mg, 1.66 mmoles) in acetone (10 ml) was stirred at room temperature for 50 minutes. After evaporation, the residue was dissolved in ethyl acetate (15 ml), washed successively with 10% aqueous sodium thiosulfate (10 ml), water (10 ml) and aqueous NaCl (10 ml), dried over sodium sulfate and evaporated to yield 494 mg (90%) of the title compound (VIIc).

IR: $\nu_{max}{}^{KBr}$ cm$^{-1}$ 3360, 3040, 3020, 2960, 1785, 1720, 1680, 1600, 1520, 1500, 1450, 1370, 1300, 1230, 1150, 1115, 1080, 990, 900, 840, 750, 700.

UV: $\lambda_{max}{}^{EtOH}$ nm(ε) 240 (24900), 260 (19400).

NMR: $\delta^{CDCl_3}$ ppm 1.30 (6H, d, J=6 Hz), 3.37 & 3.70 (1H each, d, J=16 Hz), 4.22 (2H, s), 4.55 (1H, m, J=6 Hz), 4.95 (1H, d, J=4.5 Hz), 5.83 (1H, d-d, J=4.5 & 9 Hz; d by D$_2$O), 6.66 (1H, s), 6.87 (1H, s), 7.25 (25H, s).

PREPARATION NO. 15

Diphenylmethyl 7-[(Z)-2-Allyloxyimino-2-(2-tritylaminothiazol-4-yl)acetamido]-3-chloromethyl-3-cephem-4-carboxylate (VId)

To a suspension of Compound V (1.35 g, 3 mmoles) in methylene chloride (20 ml) was added BSA (1.1 ml, 4.5 mmoles), and the mixture was stirred for 30 minutes at room temperature to become a clear solution. A mixture of (Z)-2-allyloxyimino-2-(2-tritylaminothiazol-4-yl)acetic acid (IVd) (1.40 g, 3.0 mmoles) and phosphorus pentachloride (690 mg, 3.3 mmoles) in methylene chloride (20 ml) was stirred for 15 minutes at room temperature and poured in one portion into the solution of the trimethylsilylated Compound V. The mixture was stirred for 20 minutes at room temperature and diluted with ethyl acetate (200 ml), washed with aqueous sodium bicarbonate and water, dried and evaporated under reduced pressure. The oily residue was purified by silica gel column chromatography (Wakogel, C-200, 30 g). The column was eluted with chloroform and the fractions containing the desired product were combined. Evaporation under reduced pressure afforded the title compound (VId) as an amorphous powder, yield 2.32 g (89%). Mp. 100°–115° C. (dec.).

IR: $\nu_{max}{}^{KBr}$ cm$^{-1}$ 3390, 1790, 1730, 1680, 1530, 1380, 1250, 1160, 1020.

NMR: $\delta^{CDCl_3}$ ppm 3.50 (2H, 2-H), 4.32 (2H, s, 3-CH$_2$), 4.6–6.1 (7H, m, CH$_2$CH=CH$_2$ and 6,7-H), 6.70 (1H, s, thiazole-H), 6.90 (1H, s, Ph$_2$CH), 7.1–7.6 (30H, m, phenyl protons).

Anal. Calc'd for C$_{48}$H$_{40}$N$_5$O$_5$S$_2$Cl.1/3CHCl$_3$: C, 64.05; H, 4.45; N, 7.73; S, 7.08; Cl, 7.82. Found: C, 64.13, 63.99; H, 4.61, 4.64; N, 7.50, 7.30; S, 6.85, 6.85; Cl, 7.55, 7.46.

PREPARATION NO. 16

Diphenylmethyl 7-[(Z)-2-Allyloxyimino-2-(2-tritylaminothiazol-4-yl)acetamido]-3-iodomethyl-3-cephem-4-carboxylate (VIId)

A mixture of Compound VId (2.30 g, 2.65 mmoles) and sodium iodide (2 g, 13.3 mmoles) in acetone (15 ml) was stirred for 1 hour at room temperature and then evaporated under reduced pressure. A solution of the oily residue in ethyl acetate (200 ml) was washed with 10% sodium thiosulfate and water, evaporated under reduced pressure to afford Compound VIId as an amorphous powder, which was used in the subsequent step without further purification. Yield 2.52 g (99%).

PREPARATION NO. 17

Diphenylmethyl 3-Chloromethyl-7-[(Z)-2-propargyloxyimino-2-(2-tritylaminothiazol-4-yl)acetamido]-3-cephem-4-carboxylate (VIe)

Phosphorus pentachloride (910 mg) was added to a solution of (Z)-2-propargyloxyimino-2-(2-tritylaminothiazol-4-yl)acetic acid (IVe) (1.7 g, 3.6 mmoles) in dichloromethane (30 ml). After stirring for 1 hour at room temperature the mixture was added in one portion to an ice-cooled solution of (V) (1.98 g, 4.4 mmoles) and N,O-bis(trimethylsilyl)acetamide (1.5 ml) in dichloromethane (30 ml). After stirring for 1 hour, the reaction mixture was poured into 10% aqueous NaHCO$_3$ (300 ml) and extracted with ethyl acetate (300 ml). The extract was washed with water, dried over MgSO$_4$ and evaporated under reduced pressure. The residue was chromatographed on a silica gel column. Elution with CHCl$_3$ gave the title compound [VIe] as an amorphous powder weighing 2.1 g (66%).

NMR: $\delta^{CDCl_3}$ ppm 2.45 (1H, t, CH), 3.53 (2H, d, 2-H), 4.37 (2H, s, —CH$_2$Cl), 4.83 (2H, d, O—CH$_2$C≡CH), 5.03 (1H, d, 6-H), 5.90 (1H, q, 7-H), 6.70 (1H, s, thiazole-H), 6.92 (1H, s, benzhydryl-CH).

PREPARATION NO. 18

Diphenylmethyl 7-[(Z)-2-propargyloxyimino-2-(2-tritylaminothiazol-4-yl)acetamido]-3-iodomethyl-3-cephem-4-carboxylate (VIIe)

A mixture of diphenylmethyl 3-chloromethyl-7-[(Z)-2-propargyloxyimino-2-(2-tritylaminothiazol-4-yl)acetamido]-3-cephem-4-carboxylate (VIe) (2.0 g, 2.3 mmoles) and NaI (1.04 g, 6.9 mmoles) in acetone (40 ml) was stirred for 1 hour. The mixture was filtered and the filtrate was poured into water and extracted with ethyl acetate. The organic layer was washed with 5% aqueous Na$_2$S$_2$O$_3$, water and a saturated aqueous NaCl, successively. It was then dried over MgSO$_4$ and evaporated to give 2.2 g (98%) of the title compound [VIIe].

NMR: $\delta^{CDCl_3}$ ppm 2.45 (1H, t, CH), 3.53 (2H, d, 2-H), 4.25 (2H, s, CH$_2$I), 4.83 (2H, d, O—CH$_2$), 5.0 (1H, d, 6-H), 5.80 (1H, q, 7-H), 6.70 (1H, s, thiazole-H), 6.92 (1H, s, benzhydryl-CH).

PREPARATION NO. 19

Benzhydryl 3-Iodomethyl-7-[(Z)-2-methoxyimino-2-(2-tritylaminothiazol-4-yl)acetamido]-3-cephem-4-carboxylate 1-oxide (VIIa 1-oxide)

A mixture of benzhydryl 3-iodomethyl-7-[(Z)-2-methoxyimino-2-(2-tritylaminothiazol-4-yl)acetamido]-3-cephem-4-carboxylate (VIIa) (1.10 g, 1.19 mmoles) and m-chloroperbenzoic acid (m-CPBA) (322 mg, 1.30 mmoles) in CH$_2$Cl$_2$ (22 ml) was stirred at 0° C. for 15 minutes, poured into H$_2$O (50 ml), and then extracted with CHCl$_3$ (50 ml×3). The combined extracts were washed with saturated aqueous NaHCO$_3$ (50 ml) and NaCl successively, dried and evaporated to afford the title compound (VIIa 1-oxide) (1.12 g, quantitative) as an amorphous powder.

NMR: $\delta^{CDCl_3}$ ppm 3.6 (m, 2H, 2-CH$_2$), 4.00 (s, 3H, OCH$_3$), 6.03 (dd, J=4.5, 9.6 Hz, H-7), 6.65 (s, 1H, thiazole-H), 6.92 (s, 1H, CHPh$_2$), 7.3 (m, 25H, Ph).

IR: $\nu_{max}^{KBr}$ cm$^{-1}$ 1790, 1715, 1665.

EXAMPLE 1

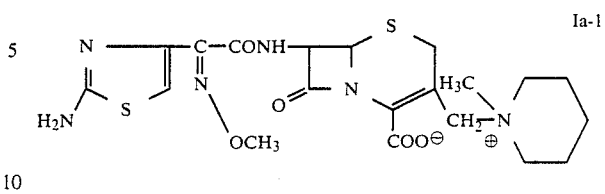

7-[(Z)-2-(2-Aminothiazol-4-yl)-2-methoxyiminoacetamido]-3-(1-methyl-1-piperidinio)methyl-3-cephem-4-carboxylate (Ia-1)

To a suspension of the 3-iodomethyl derivative VIIa (489 mg, 0.53 mmole) in ether (29 ml) was added N-methylpiperidine (0.096 ml, 0.79 mmole) and the mixture was stirred at room temperature for 1 hour. The mixture was diluted with ether (50 ml) to give a precipitate (342 mg), which was separated and treated with 90% TFA (3.5 ml) at room temperature for 1 hour. After evaporation of the solvent, the residue was triturated with ether to give the TFA salt of Ia-1 (194 mg), which was passed through an HP-20 column (50 ml), washed with H$_2$O (500 ml), and then eluted with 30% aqueous CH$_3$OH (300 ml). The eluate was evaporated and lyophilized to give crude Ia-1 (100 mg), which was a mixture of the $\Delta^3$ and $\Delta^2$ isomers in the ratio of 1.6:1.

The crude product was purified by HPLC (Lichrosorb RP-18, 8×300 mm, eluted with 0.01M ammonium phosphate buffer (pH 7.2) containing 15% CH$_3$OH]. The fractions containing the desired $\Delta^3$ isomer were collected and evaporated to a small volume, which was acidified with 1M HCl to pH 1–2 and then passed through HP-20 column (30 ml), washed with H$_2$O (500 ml) and eluted with 30% aqueous CH$_3$OH (300 ml). The eluate was evaporated and the residue lyophilized to afford the title compound (Ia-1) as a colorless powder (37 mg, 14%). Estimated purity 80% (by HPLC). Mp. 150° C. (dec.).

IR: $\nu_{max}^{KBr}$ cm$^{-1}$ 3380, 1775, 1615.

UV: $\lambda_{max}^{Phosphate\ buffer,\ pH\ 7}$ nm($\epsilon$) 235 (16300), 257 (16000).

NMR: $\delta^{D_2O}$ ppm 1.95 (6H, m, —C(CH$_2$)$_3$C—), 3.11 (3H, s, —N$^+$—CH$_3$), 3.43 (4H, m, —N$^+$—CH$_2$—), 4.10 (3H, s, OCH$_3$), 5.45 (1H, d, J=5.0, H-6), 5.95 (1H, d, J=5.0, H-7), 7.09 (1H, s, thiazole-H).

EXAMPLE 2

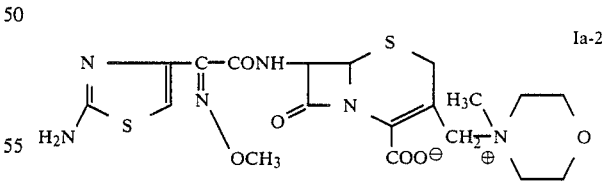

7-[(Z)-2-(2-Aminothiazol-4-yl)-2-methoxyiminoacetamido]-3-(4-methyl-4-morpholinio)methyl-3-cephem-4-carboxylate (Ia-2)

To a suspension of the 3-iodomethyl derivative VIIa (475 mg, 0.51 mmole) in ether (14 ml) was added N-methylmorpholine (0.112 ml, 1.0 mmole) and the mixture was stirred at room temperature for 1 hour. The mixture was diluted with ether (30 ml) and the resulting precipitate (318 mg) was treated with 90% TFA (3 ml) at room temperature for 1 hour. After evaporation of the solvent, the residue was triturated with ether to give the TFA salt of Ia-2 (142 mg), which was passed through an HP-20 column (50 ml), washed with H₂O (500 ml) and then eluted with 30% aqueous CH₃OH (300 ml). The eluate was evaporated and lyophilized to give crude Ia-2 (66 mg), which was a mixture of the $\Delta^3$ and $\Delta^2$ isomers in the ratio of 1.1:1. The crude preparation was purified by HPLC [Lichrosorb RP-18, 8×300 mm, eluted with 0.01M ammonium phosphate buffer (pH 7.2) containing 15% CH₃OH]. The fractions containing the desired product were collected and concentrated to a small volume. The concentrate was acidified with 1M HCl to pH 1–2 and then passed through an HP-20 column (30 ml), washed with H₂O (500 ml) and eluted with 30% aqueous CH₃OH (300 ml). The eluate was evaporated and lyophilized to afford the title compound (Ia-2). Colorless powder (30 mg, 12%). Estimated purity 83% (by HPLC). Mp. 125° C. (dec.).

IR: $\nu_{max}^{KBr}$ cm⁻¹ 3400, 1775, 1610.

UV: $\lambda_{max}^{Phosphate\ buffer,\ pH\ 7}$ nm($\epsilon$) 235 (16100), 258 (16000).

NMR: $\delta^{D2O}$ ppm 3.28 (3H, s, —N⁺—CH₃), 3.6 (4H, m, —N⁺—CH₂—), 4.12 (3H, s, OCH₃), 4.2 (4H, m, —O—CH₂—), 5.47 (1H, d, J=5.0, H-6), 5.97 (1H, d, H-7), 7.10 (1H, s, thiazole-H).

EXAMPLE 3

Ia-3

(3H, s, OCH₃), 5.44 (1H, d, J=5.0, H-6), 5.96 (1H, d, H-7), 7.10 (1H, s, thiazole-H).

EXAMPLE 4

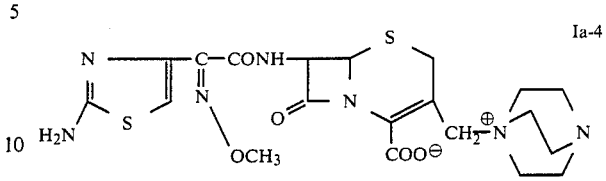

7-[(Z)-2-(2-Aminothiazol-4-yl)-2-methoxyiminoacetamido]-3-(1,4-diazabicyclo[2,2,2]octan-1-io)-methyl-3-cephem-4-carboxylate (Ia-4)

The general procedure of Example 1 was repeated except that the N-methylpiperidine used therein was replaced by 1,4-diazabicyclo[2,2,2]octane, and the title compound was thereby produced. The ratio of $\Delta^3/\Delta^2$ in the crude product was 3.1/1. The purified product (Ia-4) was obtained in 22% yield; estimated purity was 80%. Mp. >150° C. (dec.).

IR: $\nu_{max}^{KBr}$ cm⁻¹ 1775 ($\beta$-lactam CO)

UV: $\lambda_{max}^{Phosphate\ buffer,\ pH\ 7}$ nm($\epsilon$) 235 (16100), 257 (15800).

NMR: $\delta^{D2O}$ ppm 3.4 (14H, m, 2-CH₂, —N⁺—CH₂—CH₂—N—), 4.12 (3H, s, OCH₃), 5.47 (1H, d, J=5.0, H-6), 5.98 (1H, d, H-7), 7.10 (1H, s, thiazole-H).

EXAMPLE 5

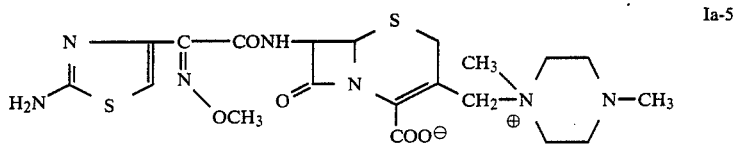

7-[(Z)-2-(2-Aminothiazol-4-yl)-2-methoxyiminoacetamido]-3-(1,4-dimethyl-1-piperazinio)methyl-3-cephem-4-carboxylate (Ia-5)

The general procedure of Example 1 was repeated except that the N-methylpiperidine utilized therein was replaced by 1,4-dimethylpiperazine, and the title compound was produced. The ratio of $\Delta^3/\Delta^2$ in the crude product was 1.3/1. The purified product (Ia-5) was obtained in 4% yield; estimated purity was 67%. Mp. >150° C. (dec.).

IR: $\nu_{max}^{KBr}$ cm⁻¹ 1780 ($\beta$-lactam CO)

UV: $\lambda_{max}^{Phosphate\ buffer,\ pH\ 7}$ nm($\epsilon$) 235 (15100), 261 (14800).

NMR: $\delta^{D2O}$ ppm 2.55 (3H, s, —N—CH₃), 3.1 (4H, m, —N—CH₂—), 3.22 (3H, s, —N⁺—CH₃), 3.6 (6H, m, 2-CH₂, —N—CH₂—), 4.13 (3H, s, OCH₃), 5.5 (1H, m, H-6), 5.95 (1H, m, H-7), 7.12 (1H, s, thiazole-H).

7-[(Z)-2-(2-Aminothiazol-4-yl)-2-methoxyiminoacetamido]-3-(1-quinuclidinio)methyl-3-cephem-4-carboxylate (Ia-3)

The general procedure of Example 1 was repeated except that the N-methylpiperidine used therein was replaced by quinuclidine (1-azabicyclo[2,2,2]octane), and the title compound was thereby produced. The ratio of $\Delta^3/\Delta^2$ in the crude product was 1.7/1. The purified product (Ia-3) was obtained in 32% yield; estimated purity was 70%. Mp. >150° C. (dec.).

IR: $\nu_{max}^{KBr}$ cm⁻¹ 1770 ($\beta$-lactam CO)

UV: $\lambda_{max}^{Phosphate\ buffer,\ pH\ 7}$ nm($\epsilon$) 235 (16300), 255 (16000).

NMR: $\delta^{D2O}$ ppm 2.1 (7H, m, —CH₂ and —CH in quinuclidine), 3.0 (8H, m, —N⁺—CH₂—, 2-CH₂), 4.12

EXAMPLE 6

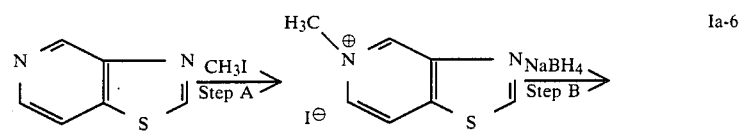

Ia-6

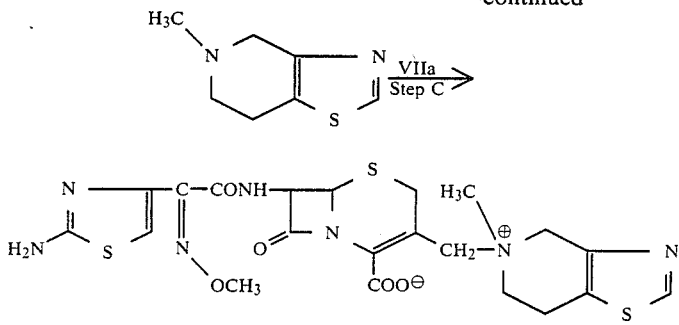

7-[(Z)-2-(2-Aminothiazol-4-yl)-2-methoxyiminoacetamido]-3-(5-methyl-4,5,6,7-tetrahydro-5-thiazolo[4,5-c]pyridinio)methyl-3-cephem-4-carboxylate (Ia-6)

(A) 5-Methylthiazolo[4,5-c]pyridinium iodide

A solution of thiazolo[4,5-c]pyridine [T. Takahashi et al., Pharm. Bull. (Japan) 2, 196 (1954)] (152 mg, 1.11 mmole) in 2 ml of methyl iodide was stirred at room temperature for 3 hours. The reaction mixture was evaporated and the residue was reprecipitated from ethanol to give 240 mg (78%) of the title compound as a pale yellow powder. Mp. 204°–205.5° C. (dec.).

IR: $\nu_{max}^{KBr}$ cm$^{-1}$ 1640, 1480, 1450, 1325, 875, 840, 830.

$^1$H-NMR: $\delta^{DMSO-d_6}$ ppm 9.83 (1H, s), 9.94 (1H, br, s), 8.87 (2H, s).

$^{13}$C-NMR: $\delta^{DMSO-d_6}$ ppm 48.0(q), 121.4(d), 149.6(s), 137.9(d), 141.4(d), 150.0(s), 165.5(d).

Analysis Calc'd. for C$_7$H$_7$N$_2$SI: C, 30.23; H, 2.54; N, 10.07; S, 11.53. Found: C, 30.44, 30.26; H, 2.40, 2.37; N, 10.21, 9.98; S, 12.10, 12.00.

(B) 5-Methyl-4,5,6,7-tetrahydrothiazolo[4,5-c]pyridine

To an ice-cooled solution of the quaternary salt prepared in Step (A) above (700 mg, 2.52 mmole) in 5 ml of water was added a solution of sodium borohydride (120 mg, 3.17 mmole) in 1.5 ml of water. After stirring for 30 minutes at room temperature, the reaction mixture was saturated with sodium carbonate and extracted with ether (3×40 ml). The ethereal extract was dried over sodium sulfate and evaporated to afford 448 mg of an oily residue, which was purified on silica gel chromatography (Wako gel C-200, 12 g). The column was eluted with methylene chloride (150 ml) and 10% methanol in methylene chloride (200 ml) and the desired fractions were combined and concentrated to obtain 331 mg (84%) of the title compound as a pale yellow oil.

IR: $\nu_{max}^{film}$ cm$^{-1}$ 2930, 2780, 1460, 1415, 1300, 1290, 1250, 1060, 910, 800.

UV: $\lambda_{max}^{EtOH}$ nm($\epsilon$) 248 (7600).

NMR: $\delta^{CDCl_3}$ ppm 2.52 (3H, s), 2.85 (4H, m), 3.68 (2H, t), 8.54 (1H, s).

Mass: m/e (%) 154(54), 153(40), 111(100), 94(10), 84(26), 58(6), 42(14).

The picrate was prepared for characterization. Mp. 149°–151° C. (dec.).

Analysis Calc'd. for C$_{13}$H$_{13}$N$_5$O$_7$S: C, 40.73; H, 3.42; N, 18.27; S, 8.36. Found: C, 41.01; 40.93; H, 3.22, 3.12; N, 17.94, 17.96; S, 8.45, 8.58.

(C) 7-[(Z)-2-(2-Aminothiazol-4-yl)-2-methoxyiminoacetamido]-3-(5-methyl-4,5,6,7-tetrahydro-5-thiazolo[4,5-c]pyridinio)methyl-3-cephem-4-carboxylate (Ia-6)

To a solution of the amine produced in Step (B) above (90 mg, 0.58 mmole) in ether (30 ml) was added the 3-iodomethylcephalosporin (VIIa), (466 mg, 0.5 mmole) and the mixture was stirred at room temperature for 40 minutes. The precipitate (324 mg) was collected by filtration, mixed with anisole (1 ml) and treated with 90% trifluoroacetic acid (5.5 ml) with ice cooling. The mixture was stirred for 1 hour at room temperature and evaporated under reduced pressure. The residue was triturated in isopropyl ether to give 263 mg of a yellow powder, which was purified by HP-20 column chromatography (40 ml). The column was eluted with water (150 ml) and 30% aqueous methanol (200 ml). The desired fractions were combined, concentrated and lyophilized to give 32 mg (18%) of the title compound (Ia-6). Estimated purity 50% (by HPLC). Mp. >161° C. (dec.).

IR: $\nu_{max}^{KBr}$ cm$^{-1}$ 1775, 1660, 1615, 1525, 1345, 1030.

UV: $\lambda_{max}^{Phosphate\ buffer,\ pH\ 7}$ nm($\epsilon$) 232 (21400).

EXAMPLE 7

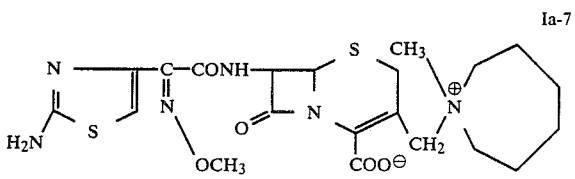

Ia-7

7-[(Z)-2-(2-Aminothiazol-4-yl)-2-methoxyiminoacetamido]-3-(1-methylhexahydroazepinio)-methyl-3-cephem-4-carboxylate (Ia-7)

Hexamethylenimine (225 μl, 2 mmoles) was added to a vigorously stirred solution of the 3-iodomethyl derivative VIIa (466 mg, 0.5 mmole) in ethyl acetate (50 ml). The mixture was stirred for 6 minutes and 0.1N HCl (20 ml) then was added with stirring. The mixture was washed with water, aqueous NaHCO$_3$ and water, successively, and evaporated under reduced pressure to give an oil (460 mg). The oil was dissolved in methyl iodide (4 ml) and allowed to stand overnight at room temperature. Ether was added to give the precipitated quaternary salt (462 mg), which was collected by filtration and treated with 90% TFA (3 ml) and anisole (0.5 ml) for 1.5 hours at room temperature. After concentration under reduced pressure and trituration with ether, the crude TFA salt was collected by filtration (300 mg, $\Delta^2/\Delta^3=\frac{1}{2}$), and was purified by HPLC (Lichrosorb RP-18, 30% CH$_3$OH). The eluate containing the desired product was concentrated and freeze-dried to give 48 mg of the title compound (Ia-7) (yield, 20%, $\Delta^2/\Delta^3=\frac{1}{2}$). Estimated purity of the $\Delta^3$ isomer, 50%.

IR: $\nu_{max}^{KBr}$ cm$^{-1}$ 1770, 1660, 1620, 1540.

UV: $\lambda_{max}^{phosphate\ buffer\ (pH\ 7)}$ nm($\epsilon$) 235 (14600), 255 (14200).

NMR: $\delta^{D2O}$ ppm 1.7–2.2 (8H, m, CH$_2$), 3.12 (3H, s, NCH$_3$), 3.3–3.7 (4H, m, CH$_2$), 4.10 (3H, s, OCH$_3$), 5.95 (1H, d, 4 Hz, 7-H), 7.08 (1H, s, thiazole-H).

EXAMPLE 8

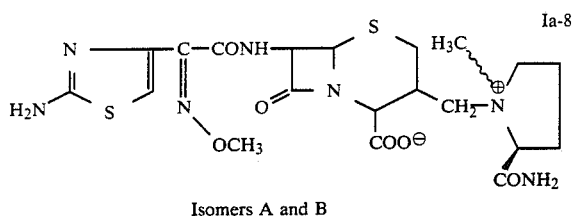

Isomers A and B

7-[(Z)-2-(2-Aminothiazol-4-yl)-2-methoxyiminoacetamido]-3-[(S)-2-carbamoyl-1-methylpyrrolidinio]methyl-3-cephem-4-carboxylate (Ia-8)

To a suspension of the 3-iodomethyl derivative VIIa (530 mg, 0.57 mmole) in ether (16 ml) was added 2-carbamoyl-1-methylpyrrolidine (145 mg, 1.14 mmole) [prepared from L-proline according to the procedure of B. J. Magerlein et al., JACS, 89 (10), 2459 (1967)], and the mixture was stirred at room temperature overnight. After the addition of ether (50 ml), the precipitate was collected by filtration to give the quaternary salt (320 mg), which was treated with 90% TFA (3 ml) at room temperature for one hour. After evaporation of the solvent, the residue was triturated with ether to give the TFA salt of Ia-8, which was passed through an HP-20 column (50 ml), washed with water (500 ml) and eluted with 30% CH$_3$OH (500 ml). The methanolic eluent was evaporated and lyophilized to give the crude product (82 mg), which was purified by HPLC (Lichrosorb RP-18, 8×300 mm, eluted with 15% methanol) to afford two diastereoisomers A and B.

Isomer A: 17 mg (6%), estimated purity, 75%. Mp. 155° C. (dec.).

IR: $\nu_{max}^{KBr}$ cm$^{-1}$ 3350, 1775, 1660, 1610.

UV: $\lambda_{max}^{phosphate\ buffer\ (pH\ 7)}$ nm($\epsilon$) 235 (16600), 257 (16000).

NMR: $\delta^{D2O}$ ppm 2.4 (4H, m, pyrrolidine-H), 3.26 (3H, s, N$^+$—CH$_3$), 4.10 (3H, s, OCH$_3$), 5.43 (1H, d, 5.0 Hz, 6-H), 5.93 (1H, d, 7-H), 7.08 (1H, s, thiazole-H).

Isomer B: 16 mg (5%), estimated purity, 65%. Mp. 155° C. (dec.).

IR: $\nu_{max}^{KBr}$ cm$^{-1}$ 3380, 1775, 1670, 1610.

UV: $\lambda_{max}^{phosphate\ buffer\ (pH\ 7)}$ nm($\epsilon$) 236 (16900), 257 (16400).

NMR: $\delta^{D2O}$ ppm 2.5 (4H, m, pyrrolidine-H), 3.11 (3H, s, N$^+$—CH$_3$), 4.10 (3H, s, OCH$_3$), 5.45 (1H, d, 5.0 Hz, 6-H), 5.95 (1H, d, 7-H), 7.08 (1H, s, thiazole-H).

EXAMPLE 9

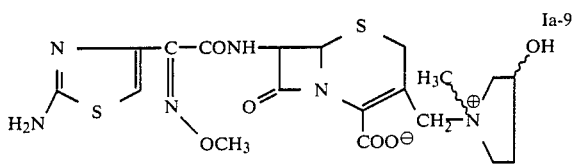

7-[(Z)-2-(2-Aminothiazol-4-yl)-2-methoxyiminoacetamido]-3-(3-hydroxy-1-methylpyrrolidinio)-methyl-3-cephem-4-carboxylate (Ia-9)

To a suspension of the 3-iodomethyl derivative VIIa (510 mg, 0.55 mmole) in ether (50 ml) was added 3-hydroxy-1-methylpyrrolidine (0.12 ml, 1.10 mmoles), and the mixture was stirred at room temperature for one hour. After the addition of ether (30 ml), the precipitate was collected by filtration to give the quaternary salt (530 mg), which was treated with 90% TFA (5 ml) at room temperature for one hour. After evaporation of the solvent, the residue was triturated with ether to give the TFA salt of Ia-9, which was chromatographed on a column of HP-20 (50 ml) by washing with water (500 ml) and subsequently eluting with 30% CH$_3$OH (500 ml). The methanolic eluent was evaporated and lyophilized to afford a crude product (145 mg), which was purified by HPLC (Lichrosorb RP-18, 8×300 mm, eluted with 10% methanol) to give the title compound (Ia-9). Yield 46 mg (17%). Estimated purity, 72%. Mp. 160° C. (dec.).

IR: $\nu_{max}^{KBr}$ cm$^{-1}$ 3320, 1770, 1610.

UV: $\lambda_{max}^{phosphate\ buffer\ (pH\ 7)}$ nm($\epsilon$) 236 (16200), 257 (15700).

NMR: $\delta^{D2O}$ ppm ca. 2.5 (2H, m, pyrrolidine-H), ca. 3.15 (3H, m, N$^+$—CH$_3$), ca. 3.7 (6H, m, —N$^+$—CH$_2$—), 4.08 (3H, s, OCH$_3$), 5.42 (1H, d, 4.8 Hz, 6-H), 5.92 (1H, d, 7-H), 7.06 (1H, s, thiazole-H).

EXAMPLE 10

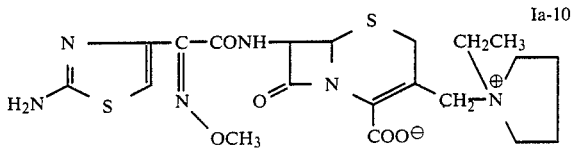

7-[(Z)-2-(2-Aminothiazol-4-yl)-2-methoxyiminoacetamido]-3-(1-ethylpyrrolidinio)methyl-3-cephem-4-carboxylate (Ia-10)

To a solution of the 3-iodomethyl cephem 1-oxide (VIIa 1-oxide) (500 mg, 0.53 mmole) in ethyl acetate (10 ml) was added 0.6M solution of 1-ethylpyrrolidine in ether (1.8 ml, 1.08 mmoles) (prepared from ethyl iodide and pyrrolidine), and the mixture was stirred at room temperature for 2 hours. After the addition of isopropyl ether (50 ml), the resulting precipitate was collected by filtration. To a solution of the quaternary salt (420 mg) in DMF (8.4 ml) were added KI (270 mg) and acetyl chloride (58 μl) and the mixture was stirred at room temperature for 2 hours, during which period the same amount of KI and acetyl chloride were added three times at 30-minute intervals. The mixture was poured into a stirred solution of 0.1M aqueous Na$_2$S$_2$O$_5$ (80 ml) and the precipitate which formed (270 mg) was collected by filtration, and treated with 90% TFA (3 ml) at room temperature for one hour. After evaporation of the solvent, the residue was triturated with ether to give the TFA salt, which was subjected to HP-20 column chromatography (30 ml), eluted with water (300 ml) and 30% methanol (300 ml). The methanolic eluate was evaporated and lyophilized to give the crude product (42 mg), which was purified by HPLC (Lichrosorb RP-18, 8×300 mm, eluted with 15% methanol) to afford the title compound (Ia-10). Yield 15 mg (6%). Estimated purity 65%. Mp. 150° C. (dec.).

IR: $\nu_{max}^{KBr}$ cm$^{-1}$ 3380, 1770, 1610.

UV: $\lambda_{max}^{phosphate\ buffer\ (pH\ 7)}$ nm($\epsilon$) 235 (16000), 257 (15400).

NMR: $\delta^{D_2O}$ ppm 1.42 (3H, t, —CH$_2$—CH$_3$), 2.2 (4H, m, pyrrolidine-H), 3.5 (6H, m, N$^+$—CH$_2$—), 4.07 (3H, s, OCH$_3$), 5.39 (1H, d, 5.0 Hz, 6-H), 5.92 (1H, d, 7-H), 7.05 (1H, s, thiazole-H).

EXAMPLE 11

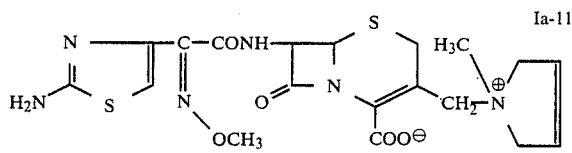

7-[(Z)-2-(2-Aminothiazol-4-yl)-2-methoxyiminoacetamido]-3-(1-methyl-3-pyrrolinio)methyl-3-cephem-4-carboxylate (Ia-11)

To a suspension of the 3-iodomethyl derivative VIIa (575 mg, 0.62 mmole) in ether (17 ml) was added 0.5M solution of 1-methyl-3-pyrroline [prepared according to the procedure of J. M. Bobbitt et al., J. Org. Chem., 25, 2230 (1960)] in ether (3 ml, 1.5 mmoles), and the mixture was stirred at room temperature for one hour. After the addition of ether (50 ml), the precipitate was collected by filtration to give the quaternary salt (565 mg), which was treated with 90% TFA (5 ml) at room temperature for one hour. After evaporation of the solvent, the residue was triturated with ether to give the TFA salt of Ia-11, which was passed through an HP-20 column (50 ml), washed with water (500 ml) and eluted with 30% CH$_3$OH (500 ml). The methanolic eluent was evaporated and lyophilized to give a crude product (160 mg), which was purified by HPLC (Lichrosorb RP-18, 8×300 mm, eluted with 10% methanol) to afford the title compound (Ia-11). Yield 35 mg (12%). Estimated purity, 65%. Mp. 140° C. (dec.).

IR: $\nu_{max}^{KBr}$ cm$^{-1}$ 3380, 1765, 1610.

UV: $\lambda_{max}^{phosphate\ buffer\ (pH\ 7)}$ nm($\epsilon$) 235 (15400), 258 (14900).

NMR: $\delta^{D_2O}$ ppm 3.25 (3H, s, N$^+$—CH$_3$), 3.77 (2H, ABq, 2-H), 4.08 (3H, s, O—CH$_3$), 4.4 (4H, m, —N$^+$—CH$_2$—), 5.41 (1H, d, 4.8 Hz, 6-H), 5.92 (1H, d, 7-H), 6.03 (2H, s, pyrroline-H), 7.05 (1H, s, thiazole-H).

EXAMPLE 12

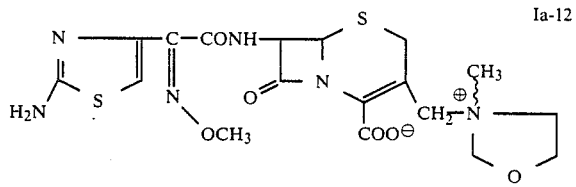

Isomers A and B

7-[(Z)-2-(2-Aminothiazol-4-yl)-2-methoxyiminoacetamido]-3-(3-methyloxazolidinio)methyl-3-cephem-4-carboxylate (Ia-12)

To a suspension of the 3-iodomethyl derivative VIIa (530 mg, 0.57 mmole) in ether (16 ml) was added 3-methyloxazolidine [prepared according to the procedure of E. D. Bergmann et al., Rec. Trav. Chim., 71, 237 (1952)] (0.1 ml, 1.15 mmoles), and the mixture was stirred at room temperature for 2.5 hours. After the addition of ether (50 ml), the precipitate was collected by filtration to give the quaternary salt (520 mg), which was treated with 90% TFA (5 ml) at room temperature for one hour. After evaporation of the solvent, the residue was triturated with ether to give the TFA salt of Ia-12, which was passed through an HP-20 column (50 ml), washed with water (500 ml) and eluted with 30% CH$_3$OH (500 ml). The methanolic eluent was evaporated and lyophilized to give a crude product (110 mg), which was purified by HPLC (Lichrosorb RP-18, 8×300 mm, eluted with 10% methanol) to afford two diastereoisomers.

From fraction 1, the isomer A (13 mg, 5%) was obtained. Estimated purity, 70%. Mp. 160° C. (dec.).

IR: $\nu_{max}^{KBr}$ cm$^{-1}$ 3380, 1770, 1660, 1610.

UV: $\lambda_{max}^{phosphate\ buffer\ (pH\ 7)}$ nm($\epsilon$) 236 (15500), 256 (14900).

NMR: $\delta^{D_2O}$ ppm 3.26 (3H, s, N$^+$—CH$_3$), 4.08 (3H, s, OCH$_3$), 5.43 (1H, d, 5.0 Hz, 6-H), 5.93 (1H, d, 7-H), 7.07 (1H, s, thiazole-H).

From fraction 2, the isomer B (17 mg, 6%) was isolated. Estimated purity, 75%. Mp. 160° C. (dec.).

IR: $\nu_{max}^{KBr}$ cm$^{-1}$ 3400, 1770, 1660, 1610.

UV: $\lambda_{max}^{phosphate\ buffer\ (pH\ 7)}$ nm($\epsilon$) 236 (15700), 256 (15100).

NMR: $\delta^{D_2O}$ ppm 3.24 (3H, s, N$^+$—CH$_3$), 4.09 (3H, s, OCH$_3$), 5.43 (1H, d, 5.0 Hz, 6-H), 5.93 (1H, d, 7-H), 7.07 (1H, s, thiazole-H).

EXAMPLE 13

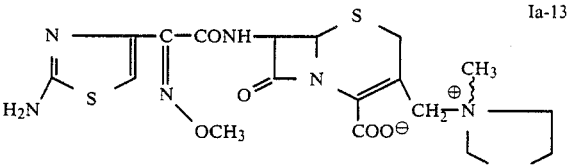

Isomers A and B

7-[(Z)-2-(2-Aminothiazol-4-yl)-2-methoxyiminoacetamido]-3-(3-methylthiazolidinio)methyl-3-cephem-4-carboxylate (Ia-13)

To a suspension of the 3-iodomethyl derivative VIIa (565 mg, 0.61 mmole) in ether (17 ml) was added a 0.2M solution of 3-methylthiazolidine [prepared according to the procedure of J. M. Lehn et al., Tetrahedron, 26, 4227 (1970)] (6.0 ml, 1.2 mmoles), and the mixture was stirred at room temperature for 1.5 hours. After the addition of ether (50 ml), the precipitate was collected by filtration to give the quaternary salt (530 mg), which was treated with 90% TFA (5 ml) at room temperature for one hour. After evaporation of the solvent, the residue was triturated with ether to give the TFA salt of Ia-13, which was passed through an HP-20 column (50 ml), washed with water (500 ml) and eluted with 30% CH₃OH (500 ml). The methanolic eluent was evaporated and lyophilized to afford a crude product (140 mg), which was purified by HPLC (Lichrosorb RP-18, 8×300 mm, eluted with 15% methanol) to give two diastereoisomers A and B.

Isomer A: 24 mg (8%). Estimated purity, 70%. Mp. 175° C. (dec.).

IR: $\nu_{max}^{KBr}$ cm$^{-1}$ 3380, 1765, 1615.
UV: $\lambda_{max}^{phosphate\ buffer\ (pH\ 7)}$ nm($\epsilon$) 235 (15700), 254 (15300).

NMR: $\delta^{D2O}$ ppm 3.4 (3H, s, N⁺—CH₃), 4.1 (3H, s, OCH₃), 5.95 (1H, m, 6-H), 7.1 (1H, s, thiazole-H).

Isomer B: 19 mg (6%). Estimated purity, 65%. Mp. 175° C. (dec.).

IR: $\nu_{max}^{KBr}$ cm$^{-1}$ 3400, 1765, 1710.
UV: $\lambda_{max}^{phosphate\ buffer\ (pH\ 7)}$ nm($\epsilon$) 235 (15600), 257 (15300).

NMR: $\delta^{D2O}$ ppm 3.28 (3H, s, —N⁺—CH₃), 4.07 (3H, s, OCH₃), 5.92 (1H, d, 5.0 Hz, 6-H), 7.05 (1H, s, thiazole-H).

EXAMPLE 14

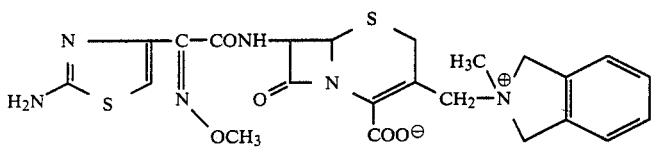

7-[(Z)-2-(2-Aminothiazol-4-yl)-2-methoxyiminoacetamido]-3-[(2-methyl-2-benzo[c]pyrrolinio)-methyl]-3-cephem-4-carboxylate (Ia-14)

To a solution of the 3-iodomethyl derivative VIIa (500 mg, 0.54 mmole) in ethyl acetate (10 ml) was added a solution of isoindoline (128 mg, 1.08 mmoles) in ethyl acetate (10 ml). After stirring for 10 minutes at room temperature, the solution was mixed with 1N HCl (12 ml). The organic layer was separated, washed with water and dried with Na₂SO₄. The solvent was evaporated, and the residue was triturated with isopropyl ether (IPE) to afford 474 mg of yellow powder. A solution of the powder (400 mg) in methyl iodide (8 ml) was allowed to stand for 3 hours at room temperature. The solution then was evaporated and the residue was triturated with IPE to give 390 mg of brown powder. A mixture of the crude powder (347 mg), anisole (0.5 ml), TFA (5 ml) and water (0.2 ml) was stirred at room temperature for 1.5 hours, and then concentrated under reduced pressure. The residue was triturated with IPE to obtain 275 mg of the crude TFA salt of Ia-14 (yellow powder), which was dissolved in water (3 ml), neutralized with sodium bicarbonate and purified by column chromatography using the packing of the PrepPAK-500/C₁₈ (Waters) (10 ml). The eluate with water (50 ml) and 20% aqueous methanol (50 ml) was fractionated, and the desired fractions were combined, concentrated and lyophilized to give 46 mg (25%) of the title compound (Ia-14) as pale yellow powder. Mp. 165°–172° C. (dec.). Estimated purity, 55%.

IR: $\nu_{max}^{KBr}$ cm$^{-1}$ 1770, 1660(sh), 1610, 1535.
UV: $\lambda_{max}^{phosphate\ buffer\ (pH\ 7)}$ nm($\epsilon$) 234 (16300), 256 (15700), 270 (13400).

NMR: $\delta^{D2O}$ ppm 3.32 (3H, s), 3.70 (2H, ABq), 4.08 (3H, s), 5.26 (1H, d, 4.5 Hz), 5.89 (1H, d, 4.5 Hz), 7.05 (1H, s), 7.51 (4H, s).

EXAMPLE 15

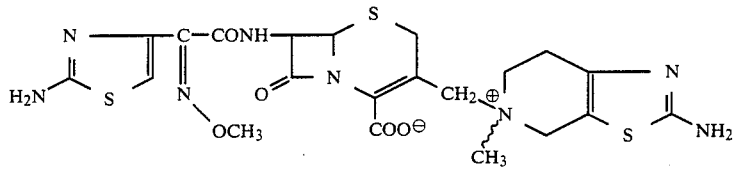

7-[(Z)-2-(2-Aminothiazol-4-yl)-2-methoxyiminoacetamido]-3-[(2-amino-4,5,7-tetrahydro-6-methyl-6-thiazolo[5,4-c]pyridinio)methyl]-3-cephem-4-carboxylate (Ia-15)

To a suspension of 2-amino-4,5,6,7-tetrahydro-6-methylthiazolo[5,4-c]pyridine [prepared according to the procedure of Dr. Karl Thomae GmbH, Neth. 6,610,324 (1/24/67); Ger. Appl. 7/23/65; C. A. 68, 49593p (1968)] (125 mg, 0.75 mmole) in ether (25 ml) was added N,O-bistrimethylsilylacetamide (0.25 ml, 1 mmole), and the mixture was stirred at room temperature for 30 minutes to make a clear solution. To the solution was added the 3-iodomethyl derivative VIIa (500 mg, 0.54 mmole) in one portion. After stirring at room temperature for 2.7 hours, the precipitate was collected by filtration to give 530 mg of the crude blocked quaternary salt as a white powder, which was mixed with anisole (2 ml), TFA (5 ml) and water (0.2 ml). The mixture was stirred at room temperature for an hour and then concentrated under reduced pressure. The residue was triturated with isopropyl ether to afford 505 mg of yellow powder, which was dissolved in a small volume of methanol. The solution was absorbed on a column of HP-20 (80 ml), which was eluted with water (200 ml), 30% CH₃OH (200 ml) and 50% CH₃OH (200 ml). Fractions containing the desired product were combined, concentrated and lyophilized to give 130 mg of powder, which was further purified by column chromatography using the packing of the PrepPAK-500/C₁₈ (Waters) (10 ml) eluted with water (50 ml) and 20% CH₃OH (50 ml). The desired fractions were combined, concentrated and lyophilized to obtain 93 mg (23%) of the title compound (Ia-15) as pale yellow powder. Estimated purity, 60%. Mp. >153° C. (dec.). The nmr indicated that this product is a mixture of the two diastereoisomers.

IR: $\nu_{max}^{KBr}$ cm$^{-1}$ 1760, 1660(sh), 1610, 1530.

UV: $\lambda_{max}^{phosphate\ buffer\ (pH\ 7)}$ nm($\epsilon$) 235 (sh, 17900), 260 (20800).

NMR: $\delta^{D2O}$ ppm 3.15 & 3.21 (a pair of s, total 3H), 4.07 (3H, s), 5.42 (1H, d, 4.5 Hz), 5.91 (1H, d, 4.5 Hz), 7.04 (1H, s).

EXAMPLE 16

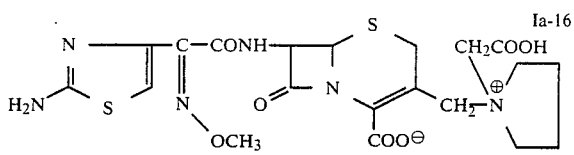

Ia-16

7-[(Z)-2-(2-Aminothiazol-4-yl)-2-methoxyiminoacetamido]-3-[1-(carboxymethyl)pyrrolidinio]-methyl-3-cephem-4-carboxylate (Ia-16)

To a solution of the 3-iodomethyl cephem 1-oxide (VIIa 1-oxide) (790 mg, 0.83 mmole) in ethyl acetate (24 ml) was added 1-(t-butoxycarbonylmethyl)pyrrolidine (310 mg, 1.67 mmoles) (prepared from t-butyl chloroacetate and pyrrolidine) and the mixture was stirred at room temperature for 2 hours. After the addition of ether (50 ml), the resulting precipitate (585 mg) was collected by filtration. To a solution of the precipitate in DMF (12 ml) were added KI (345 mg) and acetyl chloride (74 μl), and the mixture was stirred at room temperature for 2 hours, during which period the same amount of KI and acetyl chloride were added three times at 30 minute intervals. The mixture was poured into a stirred solution of 0.1M aqueous $Na_2S_2O_5$ (120 ml) and the precipitate which formed was collected by filtration (580 mg) and treated with 90% TFA (6 ml) at room temperature for one hour. After evaporation of the solvent, the residue was triturated with ether to give the TFA salt of Ia-16, which was subjected to HP-20 column chromatography (50 ml), eluted with water (500 ml) and 30% methanol (500 ml). The methanolic eluent was evaporated and lyophilized to give the crude product (80 mg), which was purified by HPLC (Lichrosorb RP-18, 8×300 mm, eluted with water) to afford the title compound of Ia-16. Yield 19 mg (4%). Estimated purity, 90%. Mp. 150° C. (dec.).

IR: $\nu_{max}^{KBr}$ cm$^{-1}$ 3380, 1765, 1615.

UV: $\lambda_{max}^{phosphate\ buffer\ (pH\ 7)}$ nm($\epsilon$) 235 (15000), 258 (15000).

NMR: $\delta^{D2O}$ ppm 2.26 (4H, m, pyrrolidine-H), 3.7 (4H, m, N$^+$—CH$_2$), 4.02 (2H, s, —CH$_2$COOH), 4.12 (3H, s, OCH$_3$), 5.45 (1H, d, 5.0 Hz, 6-$\overline{H}$), 5.97 (1H, d, 7-H), 7.11 (1H, s, thiazole-H).

EXAMPLE 17

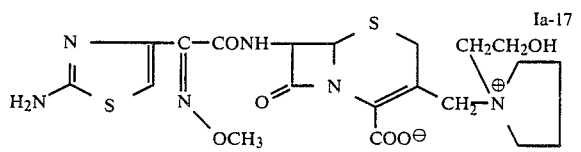

Ia-17

7-[(Z)-2-(2-Aminothiazol-4-yl)-2-methoxyiminoacetamido]-3-[(1-hydroxyethyl)pyrrolidinio]-methyl-3-cephem-4-carboxylate (Ia-17)

To a suspension of the 3-iodomethyl derivative VIIa (645 mg, 0.69 mmole) in ether (19 ml) was added 1-(2-hydroxyethyl)pyrrolidine (0.17 ml, 1.4 mmoles), and the mixture was stirred at room temperature for one hour. After the addition of ether (50 ml), the precipitate was collected by filtration to give the quaternary salt (445 mg), which was treated with 90% TFA (5 ml) at room temperature for one hour. After evaporation of the solvent, the residue was triturated with ether to give the TFA salt of Ia-17, which was passed through an HP-20 column (50 ml), washed with water (500 ml) and eluted with 30% CH$_3$OH (500 ml). The methanolic eluent was evaporated and lyophilized to afford a crude product (105 mg), which was purified by HPLC (Lichrosorb RP-18, 8×300 mm, eluted with 15% methanol) to give the title compound (Ia-17). Yield 25 mg (4%). Estimated purity, 65%. Mp. 160° C. (dec.).

IR: $\nu_{max}^{KBr}$ cm$^{-1}$ 3380, 1765, 1610.

UV: $\lambda_{max}^{phosphate\ buffer\ (pH\ 7)}$ nm($\epsilon$) 235 (15900), 257 (14900).

NMR: $\delta^{D2O}$ ppm 2.3 (4H, m, pyrrolidine-H), 3.6 (6H, m, —N$^+$—CH$_2$), 5.42 (1H, d, 5.0 Hz, 6-H), 5.94 (1H, d, 7-H), 7.08 (1H, s, thiazole-H).

EXAMPLE 18

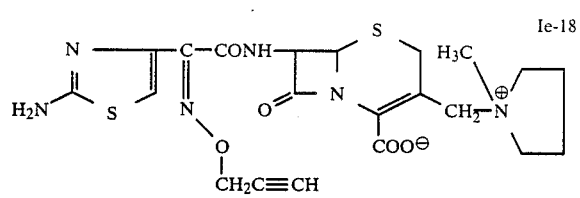

Ie-18

7-[(Z)-2-(2-Aminothiazol-4-yl)-2-propargyloxyiminoacetamido]-3-(1-methyl-1-pyrrolidiniomethyl)-3-cephem-4-carboxylate (Ie-18)

To a suspension of the iodomethyl derivative VIIe (500 mg, 0.52 mmole) in ether (50 ml) was added N-methyl pyrrolidine (89 mg, 1 mmole) and the mixture was stirred for one hour at room temperature. The reaction mixture was filtered and the filter cake (ca. 400 mg) was treated with 90% TFA (4 ml) at room temperature for one hour. The resulting mixture was concentrated under reduced pressure. The concentrate was triturated with ether to give 272 mg of the crude product, which was purified by column chromatography (HP-20, eluted with 30% methanol and 50% methanol) and HPLC (Lichrosorb RP-18, eluted with 20% methanol). The desired fractions were collected, concentrated and lyophilized to afford 24 mg (9%) of the title compound (Ie-18). Estimated purity, 70% (by HPLC). Mp. >150° C. (dec.).

UV: $\lambda_{max}^{phosphate\ buffer\ (pH\ 7)}$ nm($\epsilon$) 233 (16400), 256 (14700).

NMR: $\delta^{D2O}$ ppm 2.32 (4H, m, pyrrolidine-H), 3.05 (1H, t, 2 Hz, —C≡C$\underline{H}$), 3.10

(3H, s, H$_3$C 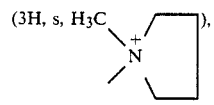), 3.64 (4H, m, pyrrolidine-H), 4.94 (2H, d, 2.0 Hz, O—C$\underline{H_2}$), 5.44 (1H, d, 5.0 Hz, 6-H), 5.84 (1H, d, 5.0 Hz, 7-H), 7.15 (1H, s, thiazole-H).

EXAMPLE 19

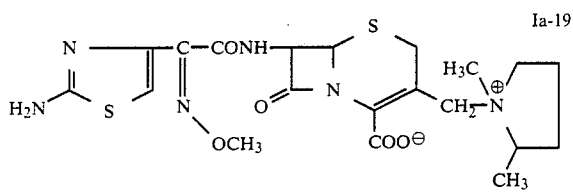

7-[(Z)-2-(2-Aminothiazol-4-yl)-2-methoxyiminoacetamido]-3-(1,2-dimethylpyrrolidinio)methyl-3-cephem-4-carboxylate (Ia-19)

To a solution of the 3-iodomethyl cephem 1-oxide (VIIa 1-oxide) (490 mg, 0.52 mmole) in ethyl acetate (15 ml) was added 1,2-dimethylpyrrolidine (0.135 ml, 1.04 mmoles), and the mixture was stirred at room temperature for one hour. After the addition of isopropyl ether (IPE) (50 ml), the resulting precipitate was collected by filtration to give the quaternary salt (430 mg), which was dissolved in DMF (9 ml) and treated with KI (275 mg, 1.66 mmoles) and acetyl chloride (59 µl, 0.83 mmole). The mixture was stirred at room temperature for 2 hours, during which period the same amount of KI and acetyl chloride were added three times at 30 minute intervals. The mixture was poured into a stirred solution of 0.1M aqueous $Na_2S_2O_5$ (90 ml) and the precipitate which formed was collected by filtration and washed with water. The product thus obtained (245 mg) was treated with 90% TFA (3 ml) at room temperature for one hour. After evaporation of the solvent, the residue was triturated with ether to give the TFA salt of Ia-19, which was subjected to HP-20 column chromatography (30 ml), eluted with water (300 ml) and 30% methanol (300 ml). The methanolic eluent was evaporated and lyophilized to give the crude product (120 mg), which was purified by HPLC (Lichrosorb RP-18, 8×300 mm, 20% methanol) to afford 56 mg (10%) of the title compound (Ia-19). Estimated purity, 60%. Mp. 150° C. (dec.).

IR: $\nu_{max}^{KBr}$ cm$^{-1}$ 3400, 1765, 1615.

UV: $\lambda_{max}^{phosphate\ buffer\ (pH\ 7)}$ nm($\epsilon$) 234 (15500), 257 (14500).

NMR: $\delta^{D_2O}$ ppm 1.48 (3H, d, 6.0 Hz, CH—CH$_3$), 2.1 (4H, m, pyrrolidine-H), 2.94 (3H, s, N$^+$—CH$_3$), 5.45 (1H, d, 4.5 Hz, 6-H), 5.90 (1H, d, 7-H), 7.05 (1H, s, thiazole-H).

EXAMPLE 20

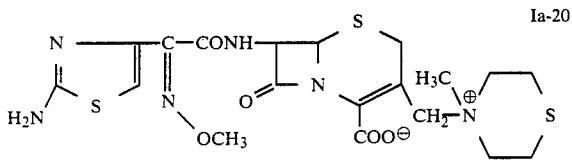

7-[(Z)-2-(2-Aminothiazol-4-yl)-2-methoxyiminoacetamido]-3-(4-methylthiomorpholinio)methyl-3-cephem-4-carboxylate (Ia-20)

To a suspension of the 3-iodomethyl derivative VIIa (570 mg, 0.61 mmole) in ether (11 ml) was added a 0.2M solution of 4-methylthiomorpholine (6.2 ml, 1.22 mmoles) [prepared according to the procedure of J. M. Lehn et al., Tetrahedron, 26, 4227 (1970)], and the mixture was stirred at room temperature for one hour. After the addition of ether (50 ml), the precipitate was collected by filtration to give the quaternary salt (560 mg). The precipitate was treated with 90% TFA (6 ml) at room temperature for one hour. After evaporation of the solvent, the residue was triturated with ether to give the TFA salt of Ia-20, which was passed through an HP-20 column (50 ml), washed with water (500 ml) and eluted with 30% CH$_3$OH (500 ml). The methanolic eluent was evaporated and lyophilized to give a crude product (160 mg), which was purified by HPLC (Lichrosorb RP-18, 8×300 mm, eluted with 15% methanol) to afford the title compound (Ia-20). Yield 30 mg (10%). Estimated purity, 65%. Mp. 140° C. (dec.).

IR: $\nu_{max}^{KBr}$ cm$^{-1}$ 3380, 1765, 1610.

UV: $\lambda_{max}^{phosphate\ buffer\ (pH\ 7)}$ nm($\epsilon$) 235 (15500), 257 (15200).

NMR: $\delta^{D_2O}$ ppm 2.95 (3H, s, N$^+$—CH$_3$), 3.1 (4H, m, —N$^+$—CH$_2$), 3.7 (2H, m, 2-H), 4.07 (3H, s, O—CH$_3$), 5.42 (1H, d, 4.5 Hz, 6-H), 5.92 (1H, d, 7-H), 7.05 (1H, s, thiazole-H).

EXAMPLE 21

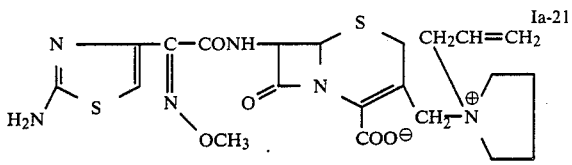

7-[(Z)-2-(2-Aminothiazol-4-yl)-2-methoxyiminoacetamido]-3-(N-allylpyrrolidinio)methyl-3-cephem-4-carboxylate (Ia-21)

Pyrrolidine (166 µl, 2 mmoles) was added to a vigorously stirred solution of the 3-iodomethyl derivative VIIa (466 mg, 0.5 mmole), and 1N HCl (5 ml) was added to quench the reaction after 4 minutes. The mixture was washed with water, aqueous NaHCO$_3$ and water, successively. Removal of the solvent under reduced pressure gave the 3-pyrrolidinomethyl derivative XXa as an oil, which was dissolved in allyl iodide (2 ml). The mixture was allowed to stand for 7 hours at room temperature and diluted with ether to precipitate the quaternary salt (500 mg), which was treated with 90% TFA (3 ml) for 1 hour at room temperature. After concentration under reduced pressure, the residue was triturated with ether to give the crude TFA salt of Ia-21 (279 mg) which was chromatographed on a column of HP-20 (1.2×20 cm, 30% CH$_3$OH). The fractions containing the desired product were collected and freeze-dried to give the crude product (76 mg), which was purified by HPLC (Lichrosorb RP-18, 20% CH$_3$OH) to give the title compound (Ia-21). Yield 17 mg (7%). Estimated purity, 70%.

IR: $\nu_{max}^{KBr}$ cm$^{-1}$ 1770, 1660, 1600, 1530.

UV: $\lambda_{max}^{phosphate\ buffer\ (pH\ 7)}$ nm($\epsilon$) 235 (15800), 258 (15000).

EXAMPLE 22

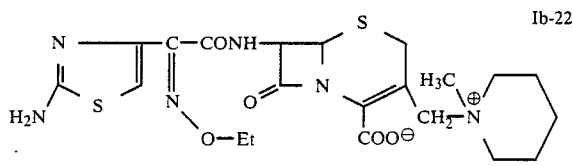

7-[(Z)-2-(2-Aminothiazol-4-yl)-2-ethox-yiminoacetamido]-3-(1-methylpiperidinio)methyl-3-cephem-4-carboxylate (Ib-22)

To a suspension of the 3-iodomethyl derivative VIIb (530 mg, 0.56 mmole) in ether (16 ml) was added N-methylpiperidine (0.14 ml, 1.13 mmoles) and the mixture was stirred at room temperature for 30 minutes. After the addition of ether (50 ml), the precipitate was collected by filtration. The quaternary salt (490 mg) was treated with 90% TFA (5 ml) at room temperature for one hour. After evaporation of the solvent, the residue was triturated with ether to give the TFA salt of Ib-22, which was passed through an HP-20 column (50 ml), washed with water (500 ml) and eluted with 30% $CH_3OH$ (500 ml). The methanolic eluent was evaporated and lyophilized to give the crude product (60 mg), which was purified by HPLC [Lichrosorb RP-18, 8×300 mm, eluted with 0.01M phosphate buffer (pH 7.2) containing 15% $CH_3OH$] and HP-20 column to afford the title compound (Ib-22). Yield 17 mg (6%). Estimated purity, 80%. Mp. 145° C. (dec.).

IR: $\nu_{max}^{KBr}$ cm$^{-1}$ 3300, 1775, 1610.

UV: $\lambda_{max}^{phosphate\ buffer\ (pH\ 7)}$ nm($\epsilon$) 237 (15300), 258 (15200).

NMR: $\delta^{D_2O}$ ppm 1.42 (3H, t, —$CH_2CH_3$), 2.0 (6H, m, piperidine-H), 3.11 (3H, s, —N$^+$—$CH_3$), 3.4 (4H, m, —N$^+$—$CH_2$—), 5.46 (1H, d, 5.0 Hz, 6-H), 5.95 (1H, d, 7-H), 7.08 (1H, s, thiazole-H).

EXAMPLE 23

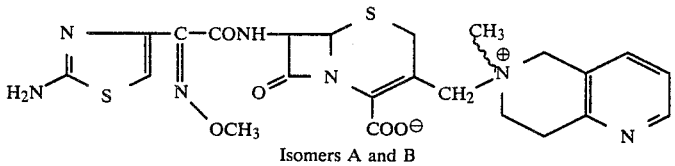

Isomers A and B

7-[(Z)-2-(2-Aminothiazol-4-yl)-2-methox-yiminoacetamido]-3-[(6-methyl-5,6,7,8-tetrahydro-6-[1,6]naphthylidinio)methyl]-3-cephem-4-carboxylate (Ia-23)

To a suspension of the 3-iodomethyl derivative VIIa (500 mg, 0.54 mmole) in 25 ml of ether was added a solution of 6-methyl-5,6,7,8-tetrahydro[1,6]naphthylidine (240 mg, 1.62 mmoles) in 5 ml of ether. The mixture was stirred at room temperature for 2.5 hours, and the resulting precipitate was collected by filtration to obtain 475 mg of crude blocked quaternary salt as pale yellow powder, which was mixed with anisole (2 ml), TFA (5 ml) and water (0.2 ml). The mixture was stirred at room temperature for an hour and concentrated. The residue was triturated with isopropyl ether to afford 442 mg of the crude TFA salt of Ia-23 as yellow powder, which was dissolved in a small volume of methanol. The solution was absorbed on a column of HP-20 (80 mg), which was eluted with water (200 ml), 30% methanol (200 ml) and 50% methanol (200 ml). Fractions containing the desired product were combined, concentrated and lyophilized to give 147 mg of powder, which was further purified by column chromatography using the packing of PrepPAK-500/$C_{18}$ (Waters) (10 ml) eluted with water (50 ml) and 20% methanol (50 ml). The desired fractions were combined, concentrated and lyophilized to obtain 108 mg of powder, which was further purified by preparative HPLC [Column, Lichrosorb RP-18; mobile phase, 25% methanol]. The eluate was divided into two fractions, and each fraction was concentrated and lyophilized. From the faster eluted fraction, 20 mg (7%) of Isomer A was obtained as pale yellow powder. Estimated purity, 50%. Mp. >160° C. (dec.).

IR: $\nu_{max}^{KBr}$ cm$^{-1}$ 1770, 1660(sh), 1610, 1535.

UV: $\lambda_{max}^{phosphate\ buffer\ (pH\ 7)}$ nm($\epsilon$) 235 (13800), 258 (14800).

NMR: $\delta^{D_2O}$ ppm 3.24 (3H, s), 4.07 (3H, s), 5.45 (1H, d, 4.5 Hz), 5.93 (1H, d, 4.5 Hz), 7.05 (1H, s), 7.60 (2H, m), 8.55 (1H, br, d).

From the slower eluted fraction, 35 mg (12%) of Isomer B was obtained as pale yellow powder. Estimated purity, 65%. Mp. >163° C. (dec.).

IR: $\nu_{max}^{KBr}$ cm$^{-1}$ 1770, 1660, 1610, 1530.

UV: $\lambda_{max}^{phosphate\ buffer\ (pH\ 7)}$ nm($\epsilon$) 236 (17200), 264 (18700).

NMR: $\delta^{D_2O}$ ppm 3.15 (3H, s), 4.06 (3H, s), 5.43 (1H, d, 4.5 Hz), 5.90 (1H, d, 4.5 Hz), 7.02 (1H, s), 7.60 (2H, m), 8.54 (1H, br, d).

We claim:

1. A compound of the formula

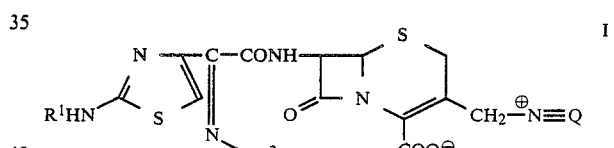

wherein $R^1$ is hydrogen or a conventional amino-protecting group, $R^2$ is a straight or branched chain alkyl, alkenyl or alkynyl group containing from 1 to 4 carbon atoms, and $$-\overset{\oplus}{N}\equiv Q$$

is a quaternary ammonio group selected from in which $R^3$ is (lower)alkyl, (lower)alkoxy(lower)alkyl, hydroxy(lower)alkyl with the provision that the hydroxy may not be on the α-carbon, carboxy(lower)alkyl, amino(lower)alkyl with the provision that the amino may not be on the α-carbon, (lower)alkenyl or halo(lower)alkyl, and

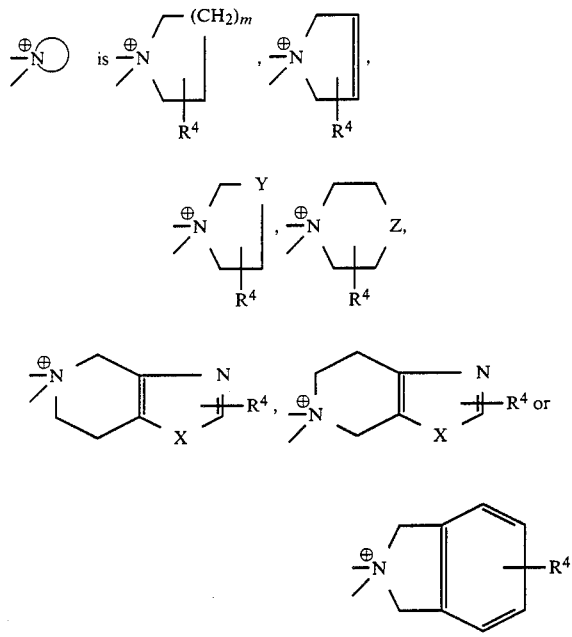

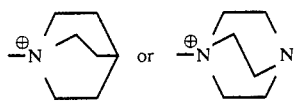

in which R⁴ is hydrogen, hydroxy, halogen, (lower)alkyl, hydroxy(lower)alkyl, (lower)alkoxy(lower)alkyl, halo(lower)alkyl, amino(lower)alkyl, (lower)alkoxy, (lower)alkylthio, (lower)alkenyl, amino, (lower)alkylamino, di(lower)alkylamino, acylamino, acyloxy, carbamoyl, amidino(lower)alkyl, phenyl, pyridyl, amidino or guanidino, m is an integer of from 1 to 3, X is sulfur or —CH=CH—, Y is oxygen or sulfur, Z is oxygen, sulfur or N—R⁵, and R⁵ is hydrogen or (lower)alkyl, with the provision that

may not be the N-methylpyrrolidinio moiety when R² is a C₁₋₄ alkyl or alkenyl group; or a nontoxic, pharmaceutically acceptable salt, physiologically hydrolyzable ester or solvate thereof.

2. A compound of claim 1 wherein R² is methyl.

3. A compound of claim 2 wherein

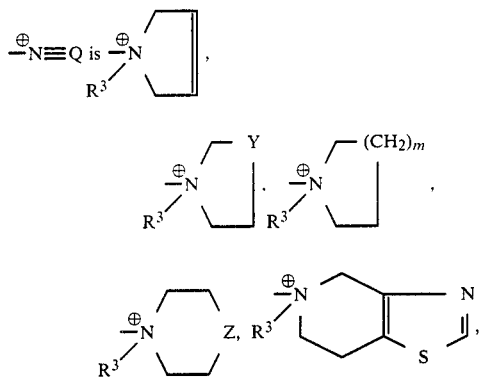

wherein m is 2 or 3, Y is oxygen or sulfur, Z is oxygen, sulfur or N—CH₃ and R³ is methyl.

4. The compound of claim 1 which is 7-[(Z)-2-(2-aminothiazol-4-yl)-2-methoxyiminoacetamido]-3-(1-methyl-1-piperidinio)methyl-3-cephem-4-carboxylate, or a nontoxic pharmaceutically acceptable salt, physiologically hydrolyzable ester or solvate thereof.

5. The compound of claim 1 which is 7-[(Z)-2-(2-aminothiazol-4-yl)-2-methoxyiminoacetamido]-3-(4-methyl-4-morpholinio)methyl-3-cephem-4-carboxylate, or a nontoxic pharmaceutically acceptable salt, physiologically hydrolyzable ester or solvate thereof.

6. The compound of claim 1 which is 7-[(Z)-2-(2-aminothiazol-4-yl)-2-methoxyiminoacetamido]-3-(1-quinuclidinio)methyl-3-cephem-4-carboxylate, or a nontoxic pharmaceutically acceptable salt, physiologically hydrolyzable ester or solvate thereof.

7. The compound of claim 1 which is 7-[(Z)-2-(2-aminothiazol-4-yl)-2-methoxyiminoacetamido]-3-(1,4-diazabicyclo[2,2,2]octan-1-io)methyl-3-cephem-4-carboxylate, or a nontoxic pharmaceutically acceptable salt, physiologically hydrolyzable ester or solvate thereof.

8. The compound of claim 1 which is 7-[(Z)-2-(2-aminothiazol-4-yl)-2-methoxyiminoacetamido]-3-(1,4-dimethyl-1-piperazinio)methyl-3-cephem-4-carboxylate, or a nontoxic pharmaceutically acceptable salt, physiologically hydrolyzable ester or solvate thereof.

9. The compound of claim 1 which is 7-[(Z)-2-(2-aminothiazol-4-yl)-2-methoxyiminoacetamido]-3-(5-methyl-4,5,6,7-tetrahydro-5-thiazolo[4,5-c]pyridinio)-methyl-3-cephem-4-carboxylate, or a nontoxic pharmaceutically acceptable salt, physiologically hydrolyzable ester or solvate thereof.

10. The compound of claim 1 which is 7-[(Z)-2-(2-aminothiazol-4-yl)-2-methoxyiminoacetamido]-3-(1-methylhexahydroazepinio)methyl-3-cephem-4-carboxylate, or a nontoxic pharmaceutically acceptable salt, physiologically hydrolyzable ester or solvate thereof.

11. The compound of claim 1 which is 7-[(Z)-2-(2-aminothiazol-4-yl)-2-methoxyiminoacetamido]-3-[(S)-2-carbamoyl-1-methylpyrrolidinio]methyl-3-cephem-4-carboxylate, or a nontoxic pharmaceutically acceptable salt, physiologically hydrolyzable ester or solvate thereof.

12. The compound of claim 1 which is 7-[(Z)-2-(2-aminothiazol-4-yl)-2-methoxyiminoacetamido]-3-(3-hydroxy-1-methylpyrrolidinio)methyl-3-cephem-4-carboxylate, or a nontoxic pharmaceutically acceptable salt, physiologically hydrolyzable ester or solvate thereof.

13. The compound of claim 1 which is 7-[(Z)-2-(2-aminothiazol-4-yl)-2-methoxyiminoacetamido]-3-(1-ethylpyrrolidinio)methyl-3-cephem-4-carboxylate, or a nontoxic pharmaceutically acceptable salt, physiologically hydrolyzable ester or solvate thereof.

14. The compound of claim 1 which is 7-[(Z)-2-(2-aminothiazol-4-yl)-2-methoxyiminoacetamido]-3-(1-methyl-3-pyrrolinio)methyl-3-cephem-4-carboxylate, or a nontoxic pharmaceutically acceptable salt, physiologically hydrolyzable ester or solvate thereof.

15. The compound of claim 1 which is 7-[(Z)-2-(2-aminothiazol-4-yl)-2-methoxyiminoacetamido]-3-(3-methyloxazolidinio)methyl-3-cephem-4-carboxylate, or a nontoxic pharmaceutically acceptable salt, physiologically hydrolyzable ester or solvate thereof.

16. The compound of claim 1 which is 7-[(Z)-2-(2-aminothiazol-4-yl)-2-methoxyiminoacetamido]-3-(3-methylthiazolidinio)methyl-3-cephem-4-carboxylate, or a nontoxic pharmaceutically acceptable salt, physiologically hydrolyzable ester or solvate thereof.

17. The compound of claim 1 which is 7-[(Z)-2-(2-aminothiazol-4-yl)-2-methoxyiminoacetamido]-3-(2-methyl-2-benzo[c]pyrrolinio)methyl-3-cephem-4-carboxylate, or a nontoxic pharmaceutically acceptable salt, physiologically hydrolyzable ester or solvate thereof.

18. The compound of claim 1 which is 7-[(Z)-2-(2-aminothiazol-4-yl)-2-methoxyiminoacetamido]-3-(2-amino-6-methyl-4,5,6,7-tetrahydro-6-thiazolo[5,4-c]pyridinio)methyl-3-cephem-4-carboxylate, or a nontoxic pharmaceutically acceptable salt, physiologically hydrolyzable ester or solvate thereof.

19. The compound of claim 1 which is 7-[(Z)-2-(2-aminothiazol-4-yl)-2-methoxyiminoacetamido]-3-[1-(carboxymethyl)pyrrolidinio]methyl-3-cephem-4-carboxylate, or a nontoxic pharmaceutically acceptable salt, physiologically hydrolyzable ester or solvate thereof.

20. The compound of claim 1 which is 7-[(Z)-2-(2-aminothiazol-4-yl)-2-methoxyiminoacetamido]-3-[(1-hydroxyethyl)pyrrolidinio]methyl-3-cephem-4-carboxylate, or a nontoxic pharmaceutically acceptable salt, physiologically hydrolyzable ester or solvate thereof.

21. The compound of claim 1 which is 7-[(Z)-2-(2-aminothiazol-4-yl)-2-propargyloxyiminoacetamido]-3-(1-methylpyrrolidinio)methyl-3-cephem-4-carboxylate, or a nontoxic pharmaceutically acceptable salt, physiologically hydrolyzable ester or solvate thereof.

22. The compound of claim 1 which is 7-[(Z)-2-(2-aminothiazol-4-yl)-2-methoxyiminoacetamido]-3-(1,2-dimethylpyrrolidinio)methyl-3-cephem-4-carboxylate, or a nontoxic pharmaceutically acceptable salt, physiologically hydrolyzable ester or solvate thereof.

23. The compound of claim 1 which is 7-[(Z)-2-(2-aminothiazol-4-yl)-2-methoxyiminoacetamido]-3-(4-methylthiomorpholinio)methyl-3-cephem-4-carboxylate, or a nontoxic pharmaceutically acceptable salt, physiologically hydrolyzable ester or solvate thereof.

24. The compound of claim 1 which is 7-[(Z)-2-(2-aminothiazol-4-yl)-2-methoxyiminoacetamido]-3-(1-allylpyrrolidinio)methyl-3-cephem-4-carboxylate, or a nontoxic pharmaceutically acceptable salt, physiologically hydrolyzable ester or solvate thereof.

25. The compound of claim 1 which is 7-[(Z)-2-(2-aminothiazol-4-yl)-2-ethoxyiminoacetamido]-3-(1-methylpiperidinio)methyl-3-cephem-4-carboxylate, or a nontoxic pharmaceutically acceptable salt, physiologically hydrolyzable ester or solvate thereof.

26. The compound of claim 1 which is 7-[(Z)-2-(2-aminothiazol-4-yl)-2-methoxyiminoacetamido]-3-(6-methyl-5,6,7,8-tetrahydro-6-[1,6]naphthylidinio)methyl-3-cephem-4-carboxylate, or a nontoxic pharmaceutically acceptable salt, physiologically hydrolyzable ester or solvate thereof.

27. The compound of claim 1 which is 7-[(Z)-2-(2-aminothiazol)-2-allyloxyiminoacetamido]-3-(1-methylpiperidinio)methyl-3-cephem-4-carboxylate, or a nontoxic pharmaceutically acceptable salt, physiologically hydrolyzable ester or solvate thereof.

28. A method of combatting bacterial infection in a warm-blooded mammal in need of such treatment comprising administering to said warm-blooded mammal an antibacterially effective amount of at least one compound of claim 1.

29. The method of claim 28 wherein the compound is 7-[(Z)-2-(2-aminothiazol-4-yl)-2-methoxyiminoacetamido]-3-(1-methyl-1-piperidinio)methyl-3-cephem-4-carboxylate, or a nontoxic pharmaceutically acceptable salt, physiologically hydrolyzable ester or solvate thereof.

30. The method of claim 28 wherein the compound is 7-[(Z)-2-(2-aminothiazol-4-yl)-2-methoxyiminoacetamido]-3-(1-quinuclidinio)methyl-3-cephem-4-carboxylate, or a nontoxic pharmaceutically acceptable salt, physiologically hydrolyzable ester or solvate thereof.

31. The method of claim 28 wherein the compound is 7-[(Z)-2-(2-aminothiazol-4-yl)-2-methoxyiminoacetamido]-3-(3-hydroxy-1-methylpyrrolidinio)methyl-3-cephem-4-carboxylate, or a nontoxic pharmaceutically acceptable salt, physiologically hydrolyzable ester or solvate thereof.

32. The method of claim 28 wherein the compound is 7-[(Z)-2-(2-aminothiazol-4-yl)-2-methoxyiminoacetamido]-3-(1-ethylpyrrolidinio)methyl-3-cephem-4-carboxylate, or a nontoxic pharmaceutically acceptable salt, physiologically hydrolyzable ester or solvate thereof.

33. The method of claim 28 wherein the compound is 7-[(Z)-2-(2-aminothiazol-4-yl)-2-methoxyiminoacetamido]-3-(1-methyl-3-pyrrolinio)methyl-3-cephem-4-carboxylate, or a nontoxic pharmaceutically acceptable salt, physiologically hydrolyzable ester or solvate thereof.

34. The method of claim 28 wherein the compound is 7-[(Z)-2-(2-aminothiazol-4-yl)-2-methoxyiminoacetamido]-3-(3-methylthiazolidinio)methyl-3-cephem-4-carboxylate, or a nontoxic pharmaceutically acceptable salt, physiologically hydrolyzable ester or solvate thereof.

35. An antibacterial composition comprising an antibacterially effective amount of at least one compound of claim 1 and an inert pharmaceutical carrier.

36. An antibacterial composition of claim 35 wherein the compound is 7-[(Z)-2-(2-aminothiazol-4-yl)-2-methoxyiminoacetamido]-3-(1-methyl-1-piperidinio)methyl-3-cephem-4-carboxylate, or a nontoxic pharmaceutically acceptable salt, physiologically hydrolyzable ester or solvate thereof.

37. An antibacterial composition of claim 35 wherein the compound is 7-[(Z)-2-(2-aminothiazol-4-yl)-2-methoxyiminoacetamido]-3-(1-quinuclidinio)methyl-3-cephem-4-carboxylate, or a nontoxic pharmaceutically acceptable salt, physiologically hydrolyzable ester or solvate thereof.

38. An antibacterial composition of claim 35 wherein the compound is 7-[(Z)-2-(2-aminothiazol-4-yl)-2-methoxyiminoacetamido]-3-(3-hydroxy-1-methylpyrrolidinio)methyl-3-cephem-4-carboxylate, or a nontoxic pharmaceutically acceptable salt, physiologically hydrolyzable ester or solvate thereof.

39. An antibacterial composition of claim 35 wherein the compound is 7-[(Z)-2-(2-aminothiazol-4-yl)-2-methoxyiminoacetamido]-3-(1-ethylpyrrolidinio)methyl-3-cephem-4-carboxylate, or a nontoxic pharmaceutically acceptable salt, physiologically hydrolyzable ester or solvate thereof.

40. An antibacterial composition of claim 35 wherein the compound is 7-[(Z)-2-(2-aminothiazol-4-yl)-2-methoxyiminoacetamido]-3-(1-methyl-3-pyrrolinio)-methyl-3-cephem-4-carboxylate, or a nontoxic pharmaceutically acceptable salt, physiologically hydrolyzable ester or solvate thereof.

41. An antibacterial composition of claim 35 wherein the compound is 7-[(Z)-2-(2-aminothiazol-4-yl)-2-methoxyiminoacetamido]-3-(3-methylthiazolidinio)-methyl-3-cephem-4-carboxylate, or a nonotoxic pharmaceutically acceptable salt, physiologically hydrolyzable ester or solvate thereof.

42. An antibacterial composition in unit dosage form comprising from about 50 mg to about 1500 mg of at least one compound of claim 1 and an inert pharmaceutical carrier.

43. An antibacterial composition in unit dosage form of claim 42 wherein the compound is 7-[(Z)-2-(2-aminothiazol-4-yl)-2-methoxyiminoacetamido]-3-(1-methyl-1-piperidinio)methyl-3-cephem-4-carboxylate, or a nontoxic pharmaceutically acceptable salt, physiologically hydrolyzable ester or solvate thereof.

44. An antibacterial composition in unit dosage form of claim 42 wherein the compound is 7-[(Z)-2-(2-aminothiazol-4-yl)-2-methoxyiminoacetamido]-3-(1-quinuclidinio)methyl-3-cephem-4-carboxylate, or a nontoxic pharmaceutically acceptable salt, physiologically hydrolyzable ester or solvate thereof.

45. An antibacterial composition in unit dosage form of claim 42 wherein the compound is 7-[(Z)-2-(2-aminothiazol-4-yl)-2-methoxyiminoacetamido]-3-(3-hydroxy-1-methylpyrrolidinio)methyl-3-cephem-4-carboxylate, or a nontoxic pharmaceutically acceptable salt, physiologically hydrolyzable ester or solvate thereof.

46. An antibacterial composition in unit dosage form of claim 42 wherein the compound is 7-[(Z)-2-(2-aminothiazol-4-yl)-2-methoxyiminoacetamido]-3-(1-ethylpyrrolidinio)methyl-3-cephem-4-carboxylate, or a nontoxic pharmaceutically acceptable salt, physiologically hydrolyzable ester or solvate thereof.

47. An antibacterial composition in unit dosage form of claim 42 wherein the compound is 7-[(Z)-2-(2-aminothiazol-4-yl)-2-methoxyiminoacetamido]-3-(1-methyl-3-pyrrolinio)methyl-3-cephem-4-carboxylate, or a nontoxic pharmaceutically acceptable salt, physiologically hydrolyzable ester or solvate thereof.

48. An antibacterial composition in unit dosage form of claim 42 wherein the compound is 7-[(Z)-2-(2-aminothiazol-4-yl)-2-methoxyiminoacetamido]-3-(3-methylthiazolidinio)methyl-3-cephem-4-carboxylate, or a nontoxic pharmaceutically acceptable salt, physiologically hydrolyzable ester or solvate thereof.

* * * * *